(12) United States Patent
Lam et al.

(10) Patent No.: US 9,073,974 B2
(45) Date of Patent: Jul. 7, 2015

(54) RGD-CONTAINING CYCLIC PEPTIDES

(75) Inventors: Kit S. Lam, Davis, CA (US); Yan Wang, Sacramento, CA (US); Wenwu Xiao, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/517,039

(22) PCT Filed: Dec. 16, 2010

(86) PCT No.: PCT/US2010/060731
§ 371 (c)(1),
(2), (4) Date: Feb. 7, 2013

(87) PCT Pub. No.: WO2011/079015
PCT Pub. Date: Jun. 30, 2011

(65) Prior Publication Data
US 2013/0172270 A1    Jul. 4, 2013

Related U.S. Application Data

(60) Provisional application No. 61/288,585, filed on Dec. 21, 2009.

(51) Int. Cl.
| C07K 7/50 | (2006.01) |
|---|---|
| A61K 38/12 | (2006.01) |
| C07K 7/64 | (2006.01) |
| C07K 14/78 | (2006.01) |
| A61K 38/00 | (2006.01) |

(52) U.S. Cl.
CPC . *C07K 7/64* (2013.01); *A61K 38/00* (2013.01); *C07K 14/78* (2013.01)

(58) Field of Classification Search
CPC ....... A61K 38/00; A61K 38/08; A61K 38/12; C07K 7/64; C07K 14/78
See application file for complete search history.

(56) References Cited

U.S. PATENT DOCUMENTS

| 5,759,996 | A | 6/1998 | Cheng et al. |
|---|---|---|---|
| 5,837,218 | A * | 11/1998 | Peers et al. .................. 424/1.69 |
| 2005/0202507 | A1 | 9/2005 | Landis et al. |
| 2008/0033003 | A1 | 2/2008 | Pisano et al. |

FOREIGN PATENT DOCUMENTS

| WO | WO 92/00995 A1 * | 1/1992 | ............... C07K 7/00 |
|---|---|---|---|
| WO | WO 94/29349 A1 * | 12/1994 | ............. C07K 15/00 |

OTHER PUBLICATIONS

Adessi et al, Converting a Peptide into a Drug: Strategies to Improve Stability and Bioavailability, Current Medicinal Chemistry, 2002, pp. 963-978.*
Xiao et al, Discovery of novel RGD ligands against alpha v beta 3 integrin with one-bead one-compound combinatorial library, 2009 AACR Annual Meeting, Apr. 2009, p. 1.*
Xiao et al, The use of one-bead one-compound combinatorial library technology to discover high-affinity αvβ3 integrin and cancer targeting RGD ligands with a build-in handle, Mol Cancer Ther, 2010, 9, pp. 2714-2723.*
Kantlehner et al, Surface coating with cyclic RGD peptides stimulates osteoblast adhesion and proliferation as well as bone formation, Chembiochem, 2000, 1, pp. 107-114.*
International Search Report and Written Opinion dated Feb. 18, 2011, issued in related International Patent Application No. PCT/US2010/060731, filed Dec. 16, 2010.
Cardarelli et al., "Cyclic RGD Peptide Inhibits α4β1 Interaction with Connecting Segment 1 and Vascular Cell Adhesion Molecule," 1994, vol. 269, No. 28, pp. 18668-18673.
Gehlsen et al., "Inhibition of In Vitro Tumor Cell Invasion by Arg-Gly-Asp-containing Synthetic Peptides," 1988, J. of Cell Biology, vol. 106, pp. 925-930.
Hsiong et al., "AFM Imagining of RGD Presenting Synthetic Extracellular Matrix Using Gold Nanoparticles," 2008, Macromol. Biosci. vol. 8, pp. 469-477.

* cited by examiner

*Primary Examiner* — Julie Ha
*Assistant Examiner* — Li Ni Komatsu
(74) *Attorney, Agent, or Firm* — Kilpatrick Townsend & Stockton LLP

(57) ABSTRACT

The present invention is drawn to cyclic RGD peptides linked via a disulfide bond, where the terminal cysteines are preferably in the D configuration. These peptides target αvβ3 integrin on tumor cells and neovasculatures and function as targeting agents for tumor diagnostic imaging and therapy. Compared with the commonly used RGD ligands, compounds of the present invention have improved targeting efficacy and lower nonspecific binding to normal organs. Moreover, the compounds of the present invention can be functionalized to conjugate imaging payload without decreasing binding strength.

9 Claims, 11 Drawing Sheets

(a)

(b)

Uptake of Biotinylated RGD Peptides by U-87 MG Tumor

```
                            SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: synthetic nonapeptide ligand selective for
      alphav integrin

<400> SEQUENCE: 1

Cys Asp Cys Arg Gly Asp Cys Phe Cys
1               5

<210> SEQ ID NO 2
<211> LENGTH: 4
<212> TYPE: PRT
<213> ORGANISM: Artificial Sequence
<220> FEATURE:
<223> OTHER INFORMATION: synthetic cyclic peptide cyclo(RGD-(NMe)V-)
      binding selectively to alphavbeta3 integrin
<220> FEATURE:
<221> NAME/KEY: MOD_RES
<222> LOCATION: (1)...(1)
<223> OTHER INFORMATION: Arg cyclized peptide bond to Nalpha-methyl-
      valine at position 4
<220> FEATURE:
<221> NAME/KEY: MOD_RES
<222> LOCATION: (4)...(4)
<223> OTHER INFORMATION: Nalpha-methyl-valine cyclized peptide bond to
      Arg at position 1

<400> SEQUENCE: 2

Arg Gly Asp Val
1
```

RGD-CONTAINING CYCLIC PEPTIDES

CROSS-REFERENCE TO RELATED APPLICATIONS

This application is the U.S. National Stage entry under §371 of International Application No. PCT/US2010/060731, filed Dec. 16, 2010, which claims priority to U.S. Provisional Application No. 61/288,585, filed Dec. 21, 2009, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. CA115483 and CA135345, awarded by the National Institutes of Health. The Government has certain rights in this invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file -2008-1.TXT, created on Mar. 7, 2013, 4,096 bytes, machine format IBM-PC, MS-Windows operating system, is hereby incorporated by reference in its entirety for all purposes.

BACKGROUND OF THE INVENTION

αvβ3 integrin serves as a receptor for a variety of extracellular matrix proteins displaying the arginine-glycine-aspartic acid (RGD) tripeptide sequence. These proteins include vitronectin, fibronectin, fibrinogen, laminin, collagen, Von Willibrand's factor, osteoponin, and adenovirus particles (Jin, H. and J. Varner, Br. J. Cancer, 2004. 90(3): p. 561-5). αvβ3 integrin, expressed on the surface of various normal and cancer cell types, is involved in multiple physiological processes including angiogenesis, apoptosis, and bone resorption. During angiogenesis, attachment of endothelial αvβ3 integrin to the extracellular matrix is required for the survival and maturation of newly forming blood vessels and ligands against αvβ3 integrin induce apoptosis of angiogenic vascular cells, leaving pre-existing quiescent blood vessels unaffected. In addition, αvβ3 integrin has been observed to be over-expressed on metastatic tumor cells such as malignant melanoma and glioblastoma. Since integrin plays a key role in angiogenesis and metastasis of human tumors, αvβ3 integrin ligands are of great interest to advances in targeted-therapy and cancer imaging.

RGD motif was described in early 1980's by several groups such as Michael D. Pierschbacher and Erkki Ruoslahti (Pierschbacher, M. D. and E. Ruoslahti, Nature, 1984. 309 (5963): p. 30-3). Since then, many RGD analogues have been designed and synthesized (Haubner R., G. R., Diefenbach B., Goodman S. L., Jonczyk A., Kessler H., J. Am. Chem. Soc., 1996. 118(32): p. 13). Many naturally occurring snake venoms also contain the RGD motif (Markland, F. S., Toxicon, 1998. 36(12): p. 1749-8000). Phage-display peptide library screening has been used to identify peptide ligands targeting various integrins, thereby elucidating unique integrin or tissue targeting peptides. Using this screening methodology, the nonapeptide, CDCRGDCFC (SEQ ID NO:1), was identified to be highly selective against αv integrins (Koivunen, E., B. Wang, and E. Ruoslahti, Biotechnology (NY), 1995. 13(3): p. 265-70). Another "design approach" based on "spatial screening" of cyclopeptides, in which conformational restriction is induced by variation of the ring size, amino acid chirality and retro-inverso structures, N-methylation of peptide backbone, or introduction of constraining structural elements, have led to the discovery of Cilengitide (Haubner R., G. R., Diefenbach B., Goodman S. L., Jonczyk A., Kessler H., J. Am. Chem. Soc., 1996. 118(32): p. 13 and Dechantsreiter, M. A., et al.,. J Med Chem, 1999. 42(16): p. 3033-40). This cyclic peptide, cyclo(RGD-(NMe)V-) (SEQ ID NO:2), binds strongly and relatively selectively to αvβ3 integrin, and is now in clinical trials for the treatment of several different kinds of cancers (Friess, H., et al., BMC Cancer, 2006. 6: p. 285.; Hariharan, S., et al., Ann Oncol, 2007. 18(8): p. 1400-7; MacDonald, T. J., et al., J. Clin. Oncol., 2008. 26(6): p. 919-24.; and Nabors, L. B., et al., J. Clin. Oncol., 2007. 25(13): p. 1651-7). Some other cyclopeptides and their derivatives which bind integrin are disclosed in U.S. Pat. No. 6,610,826. However, due to intrinsic constraints of these screening processes, only L-amino acid residues can be included in the phage display peptide libraries and the number of peptides that can be simultaneously tested in the "spatial screening" process is rather limited.

There is a need for better and different binding agents of αvβ3 integrin that can have improved targeting efficacy, lower nonspecific binding to normal organs and carry payloads of therapeutics and/or diagnostics. Surprisingly, the present invention satisfies this and other needs.

BRIEF SUMMARY OF THE INVENTION

In one embodiment, the present invention provides compounds of formula (I):

$$X_1\text{-}X_2\text{-}X_3\text{-}X_4\text{-}X_5\text{-}X_6\text{-}X_7\text{-}X_8 \qquad (I).$$

Radicals $X_1$, $X_2$, $X_6$, $X_7$ and $X_8$ of the compound of formula (I) are each independently an amino acid. At least one of radicals $X_1$, $X_2$, $X_6$, $X_7$ and $X_8$ is a D-amino acid. Radical $X_3$ of formula (I) is a basic amino acid, while radical $X_4$ is Gly, and radical $X_5$ is an acidic amino acid. Moreover, the compounds of formula (I) are peptides cyclized via a disulfide or a diselenium bond between amino acids $X_1$ and $X_8$.

In another embodiment, the present invention provides a pharmaceutical composition having a compound of formula (I) and a pharmaceutically acceptable excipient.

In other embodiments, the present invention provides a method of inhibiting αvβ3 integrin, including contacting the αvβ3 integrin with an amount of a compound of formula (I) sufficient to inhibit the activity of the αvβ3 integrin.

BRIEF DESCRIPTION OF THE DRAWINGS

FIG. 3a shows integrin transfected K562 cells stained with LXW7. Samples labeled A were sequentially treated with 1 µM LXW7-Bio and Streptavidin-PE and detected with Flow Cytometry. Samples labeled B depict samples without treatment of LXW7-Bio and as negative controls. LXW7 showed strong positive binding with αvβ3, weak cross-reaction with αIIbβ3, no binding with α1, α2, α3, α4, α5, α6 and α9. FIG. 3b shows integrin transfected K562 cells stained with LXW64. Samples labeled C: cells were treated with 1 µM LXW64-Biotin and Streptavidin-PE successively, and measured with Flow Cytometry. Samples labeled D represent cells without treatment of 64-Biotin and as negative controls. LXW64 showed significant positive binding with αvβ3, weak cross-reaction with αvβ5 and αIIbβ3, and no binding with α5β1.

DETAILED DESCRIPTION OF THE INVENTION

I. General

Figure 1:
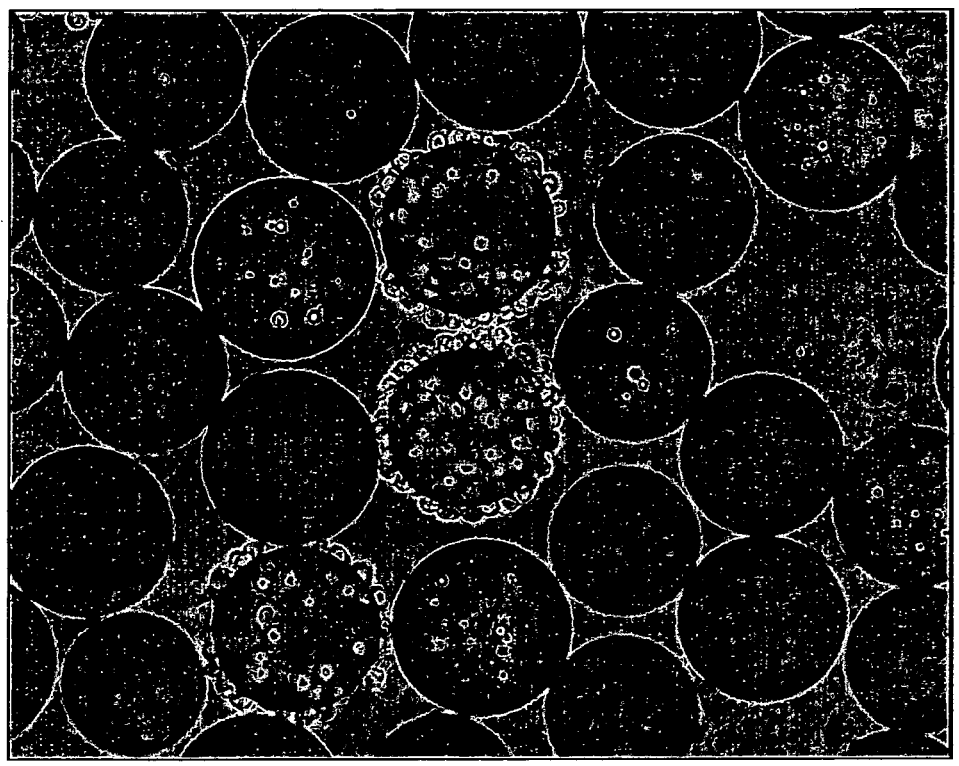
FIG. 1 shows Library 1 screened with αvβ3-K562 cells. Some positive binding beads were covered by αvβ3-K562 cells within 1 hour. Scale bar=100 µM.

The present invention is drawn to cyclic RGD peptides linked via a disulfide bond, where the terminal cysteines are preferably in the D configuration. These peptides target αvβ3 integrin on tumor cells and neovasculatures and function as targeting agents for tumor diagnostic imaging and therapy. Compared with the commonly used RGD ligands, compounds of the present invention have improved targeting efficacy and lower nonspecific binding to normal organs. Moreover, the compounds of the present invention can be functionalized to conjugate imaging payload without decreasing binding strength.

II. Definitions

As used herein, the following terms have the meanings ascribed to them unless specified otherwise.

The term "amino acid" refers to naturally-occurring α-amino acids and their stereoisomers, as well as unnatural amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid.

Amino acids may be referred to herein by either their commonly known three letter symbols or by the one-letter symbols recommended by the IUPAC-IUB Biochemical Nomenclature Commission. For example, an L-amino acid may be represented herein by its commonly known three letter symbol (e.g., Arg for L-arginine) or by an upper-case one-letter amino acid symbol (e.g., R for L-arginine). A D-amino acid may be represented herein by its commonly known three letter symbol with "D" as prefix (e.g., DArg, D-Arg or DArg for D-arginine) or by a lower-case one-letter amino acid symbol (e.g., r for D-arginine).

Amino acids can be characterized by at least one of several properties. For example, amino acids can be basic, acidic,-polar or hydrophobic. Basic amino acids are those having a basic or positively charged side chain at pH values below the pKa, and include, but are not limited to, Lys, Arg, HoArg, Agp, Agb, Dab, Dap and Orn and stereoisomers thereof. Acidic amino acids are those having an acidic or negatively charged side chain at physiological pH, and include, but are not limited to, Asp, Glu, Aad, Bec and stereoisomers thereof. Basic amino acids can generally be referred by the symbol "$X^+$" and acidic amino acids by "$X^−$". Polar amino acids generally refer to those having a polar and uncharged side chain and include, but are not limited to, Asn, Ser, Thr, Gln. Similarly, hydrophobic amino acids generally refer to those having a hydrophobic side chain and include, but are not limited to, Val, Leu, Ile, Met, and Phe. One of skill in the art will appreciate that other basic and acidic amino acids are known in the art.

With respect to amino acid sequences, one of skill in the art will recognize that individual substitutions, additions, or deletions to a peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins*, 1984).

The term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 10 amino acids in length.

The term "cancer" refers to any of various malignant neoplasms characterized by the proliferation of anaplastic cells that tend to invade surrounding tissue and metastasize to new body sites. Examples of different types of cancer suitable for treatment using the compounds and methods of the present invention are described below.

The term "therapeutically effective amount or dosage" refers to the amount of a compound of the present invention that is capable of achieving a therapeutic effect in a subject in need thereof. For example, a therapeutically effective amount of a compound of the present invention can be the amount that is capable of preventing or relieving one or more symptoms associated with cancer or an inflammatory or autoimmune disease. One skilled in the art will appreciate that the compounds of the present invention can be co-administered with other therapeutic agents (e.g., ions, small organic molecules, peptides, proteins, polypeptides, oligosaccharides, etc.) such as anti-cancer, anti-inflammatory, or immunosuppressive agents.

The term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a compound of the present invention for preventing or relieving one or more symptoms associated with cancer or an inflammatory or autoimmune disease. By "co-administer" it is meant that a compound of the present invention is administered at the same time, just prior to, or just after the administration of a second drug (e.g., anti-cancer agent, anti-inflammatory agent, immunosuppressive agent, etc.).

The term "disulfide bond" includes the covalent bond formed between two sulfur atoms. Some amino acids comprise a sulfur atom that can form a disulfide bond or bridge with another sulfur atom. This bond is usually derived by the coupling of two thiol groups.

The term "diselenium bond" includes the covalent bond formed between two selenium atoms. Some unnatural amino acids may comprise a selenium atom that can form a diselenium bond with another selenium atom.

The term "inhibit" refers to a decrease, whether partial or whole, in a specific action or function. When used in connection with enzymatic activity, refers generally to inhibiting the enzymatic activity by at least about 50%.

The term "bind" includes any physical or chemical attachment or close association, which may be permanent or temporary.

The term "contacting" refers to the process of bringing into contact at least two distinct species such that they can react. It should be appreciated, however, the resulting reaction product can be produced directly from a reaction between the added reagents or from an intermediate from one or more of the added reagents which can be produced in the reaction mixture.

The term "treating" describes the management and care of a patient for the purpose of combating the disease, condition, or disorder and includes the administration of a composition of this invention to prevent the onset of the symptoms or complications, alleviating the symptoms or complications, or eliminating the disease, condition, or disorder.

The term "$\alpha v \beta 3$ integrin" refers to a receptor of vitronectin. $\alpha v \beta 3$ integrin serves as a receptor for a variety of extracellular matrix proteins displaying the arginine-glycine-aspartic acid (RGD) tripeptide sequence. These proteins include vitronectin, fibronectin, fibrinogen, laminin, collagen, Von Willibrand's factor.

The term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "lower" referred to above and hereinafter in connection with organic radicals or compounds respectively defines a compound or radical which can be branched or unbranched with up to and including 7, preferably up to and including 4 and (as unbranched) one or two carbon atoms.

As used herein, the term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —$(CH_2)_n$—, where n is 1, 2, 3, 4, 5 or 6. Alkylene groups include, but are not limited to, methylene, ethylene, propylene, isopropylene, butylene, isobutylene, sec-butylene, pentylene and hexylene.

As used herein, the term "alkoxy" refers to an alkyl group having an oxygen atom that connects the alkyl group to the point of attachment. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "haloalkoxy" group.

As used herein, the term "heteroalkyl" refers to an alkyl group having from 1 to 3 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heteroalkyl can include ethers, thioethers and alkyl-amines.

As used herein, the term "haloalkyl" refers to alkyl as defined above where some or all of the hydrogen atoms are substituted with halogen atoms. Halogen (halo) preferably represents chloro or fluoro, but may also be bromo or iodo. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "halo-alkoxy" refers to an alkoxy group having at least one halogen. Halo-alkoxy is as defined for alkoxy where some or all of the hydrogen atoms are substituted with halogen atoms. The alkoxy groups can be substituted with 1, 2, 3, or more halogens. When all the hydrogens are replaced with a halogen, for example by fluorine, the compounds are per-substituted, for example, perfluorinated. Halo-alkoxy includes, but is not limited to, trifluoromethoxy, 2,2,2,-trifluoroethoxy, perfluoroethoxy, etc.

As used herein, the term "halogen" refers to fluorine, chlorine, bromine and iodine.

As used herein, the term "cycloalkyl" refers to a saturated or partially unsaturated, monocyclic, fused bicyclic or bridged polycyclic ring assembly containing from 3 to 12 ring atoms, or the number of atoms indicated Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, $C_{3-8}$cycloalkyl includes cyclopropyl, cyclobutyl, cyclopentyl, cyclohexyl, cyclooctyl, and norbornane.

As used herein, the term "alkyl-cycloalkyl" refers to a radical having an alkyl component and a cycloalkyl component, where the alkyl component links the cycloalkyl component to the point of attachment. The alkyl component is as defined above, except that the alkyl component is at least divalent in order to link to the cycloalkyl component and to the point of attachment. In some instances, the alkyl component can be absent. The cycloalkyl component is as defined within. Examples of alkyl-cycloalkyl include methylene-cyclohexane, among others.

As used herein, the term "heterocycloalkyl" refers to a ring system having from 3 ring members to about 20 ring members and from 1 to about 5 heteroatoms such as N, O and S. Additional heteroatoms can also be useful, including, but not limited to, B, Al, Si and P. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

As used herein, the term "alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent in order to link to the heterocycloalkyl component and to the point of attachment. In some instances, the alkyl component can be absent. The heterocycloalkyl component is as defined above. Examples of alkyl-heterocycloalkyl include methylene-piperidinyl, among others.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

As used herein, the term "alkyl-aryl" refers to a radical having an alkyl component and an aryl component, where the alkyl component links the aryl component to the point of attachment. The alkyl component is as defined above, except that the alkyl component is at least divalent in order to link to the aryl component and to the point of attachment. In some instances, the alkyl component can be absent. The aryl component is as defined above. Examples of alkyl-aryl groups include, but are not limited to, benzyl.

As used herein, the term "Heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Similarly, substituents for the aryl and heteroaryl groups are varied and are selected from: -halogen, —OR', —OC(O)R', —NR'R", —SR', —R', —CN, —NO₂, —CO₂R', —CONR'R", —C(O)R', —OC(O)NR'R", —NR"C(O)R', —NR"C(O)₂R', —NR'—C(O)NR"R"', —NH—C(NH₂)═NH, —NR'C(NH₂)═NH, —NH—C(NH₂)═NR', —S(O)R', —S(O)₂R', —S(O)₂NR'R", —N₃, —CH(Ph)₂, perfluoro(C₁-C₄)alkoxy, and perfluoro(C₁-C₄)alkyl, in a number ranging from zero to the total number of open valences on the aromatic ring system; and where R', R" and R'" are independently selected from hydrogen, (C₁-C₈)alkyl and heteroalkyl, unsubstituted aryl and heteroaryl, (unsubstituted aryl)-(C₁-C₄)alkyl, and (unsubstituted aryl)oxy-(C₁-C₄)alkyl.

As used herein, the term "alkyl-heteroaryl" refers to a radical having an alkyl component and a heteroaryl component, where the alkyl component links the heteroaryl component to the point of attachment. The alkyl component is as defined above, except that the alkyl component is at least divalent in order to link to the heteroaryl component and to the point of attachment. In some instances, the alkyl component can be absent. The heteroaryl component is as defined within. Examples of alkyl-heteroaryl include methylene-pyridyl, among others.

III. Cyclic Peptides

The present invention describes cyclic RGD-peptides. In some embodiments, the present invention provides compounds of formula (I):

$$X_1\text{-}X_2\text{-}X_3\text{-}X_4\text{-}X_5\text{-}X_6\text{-}X_7\text{-}X_8 \qquad (I)$$

Radicals $X_1$, $X_2$, $X_6$, $X_7$ and $X_8$ of the compound of formula (I) are each independently an amino acid. At least one of radicals $X_1$, $X_2$, $X_6$, $X_7$ and $X_8$ is a D-amino acid. Radical $X_3$ of formula (I) is a basic amino acid, while radical $X_4$ is Gly, and radical $X_5$ is an acidic amino acid. Moreover, the compounds of formula (I) are peptides cyclized via a disulfide or a diselenium bond between amino acids $X_1$ and $X_8$.

The compounds of formula (I) can include basic amino acids, such as those having a positively charged side chain. Non-limiting examples of basic amino acids are Lys, Arg, HoArg, Agp, Agb, Dab, Dap and Orn, and stereoisomers thereof. The compounds of formula (I) can also include acidic amino acids, such as those with a negatively charged side chain. Non-limiting examples of acidic amino acids are Asp, Glu, Aad, and Bec, and stereoisomers thereof. Basic amino acids can generally be referred by the symbol "X⁺" and acidic amino acids by "X⁻". One of skill in the art will appreciate that other basic and acidic amino acids are known in the art.

Amino acids useful in the compounds of the present invention include naturally-occurring amino acids, as well as those amino acids that are later modified, e.g., γ-carboxyglutamate and O-phosphoserine, as well as unnatural amino acids. Naturally-occurring α-amino acids include (shown with the corresponding 3 letter and single letter codes), without limitation, alanine (Ala, A), cysteine (Cys, C), aspartic acid (Asp, D), glutamic acid (Glu, E), phenylalanine (Phe, F), glycine (Gly, G), histidine (His, H), isoleucine (Ile, I), arginine (Arg, R), lysine (Lys, K), leucine (Leu, L), methionine (Met, M), asparagine (Asn, N), proline (Pro, P), glutamine (Gln, Q), serine (Ser, S), threonine (Thr, T), valine (Val, V), tryptophan (Trp, W) and tyrosine (Tyr, Y). Stereoisomers of a naturally-occurring α-amino acids include, without limitation, D-alanine (DAla, a), D-cysteine (DCys, c), D-aspartic acid (DAsp, d), D-glutamic acid (DGlu, e), D-phenylalanine (DPhe, f), D-histidine (DHis, h), D-isoleucine (DIle, i), D-arginine (DArg, r), D-lysine (DLys, k), D-leucine (DLeu, l), D-methionine (DMet, m), D-asparagine (DAsn, n), D-proline (DPro, p), D-glutamine (DGln, q), D-serine (DSer, s), D-threonine (D-Thr, t), D-valine (D-Val, v), D-tryptophan (DTrp, w) and D-tyrosine (DTyr, y).

Unnatural amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" are unnatural amino acids that have the same basic chemical structure as naturally-occurring amino acids, i.e., an α carbon that is bound to a hydrogen, a carboxyl group, an amino group, but have modified R (i.e., side-chain) groups. Suitable unnatural amino acids include, without limitation, α-aminohexanedioic acid (Aad), acid (Abu), 3-aminobenzoic acid (3Abz), azetidine-2-carboxylic acid (Aca), 1-aminocyclobutane-1-carboxylic acid (Acb), α-amino-3-chloro-4,5-dihydro-5-isoazoleacetic acid (Acdi), 4-amino-4-carboxy-1,1-dioxo-tetrahydrothiopyran (Acdt), 1-amino-1-cyclohexane carboxylic acid (Ach), 1-aminocyclopentane-1-carboxylic acid (Acp), 1-aminocyclopropane-1-carboxylic acid (Acpc), 4-amino-4-carboxytetrahydropyran (Actp), 8-amino-1,4-dioxaspiro[4.5]decane-8-carboxylic acid (Aecc), (S)-2-amino-4-guanidino-butanoic acid (Agb), allylglycine (Agl), (S)-2-amino-3-guanidino-propanoic acid (Agp), 2-aminoheptanoic acid (Aha), 1-amino-1-(4-hydroxycyclohexyl)carboxylic acid (Ahch), α-aminoisobutyric acid (Aib), 2-aminoindane-2-carboxylic acid (Aic), 1-amino-1-(4-ketocyclohexyl)carboxylic acid (Akch), 2-aminooctanoic acid (Aoa), 2-amino-2-naphthylacetic acid (Ana), 1-amino-1-(3-piperidinyl) carboxylic acid (3Apc), 1-amino-1-(4-piperidinyl) carboxylic acid (4Apc), 2-amino-3-(4-piperidinyl) propionic acid (4App), homoarginine (HoArg), Nα-methyl-arginine ((NMe)Arg), Na-methyl-aspartic acid ((NMe)Asp), α-aminooctanedioic acid (Asu), (R)-2-amino-3-(2-carboxyethylsulfanyl)propanoic acid (Bec), 4,4'-biphenylalanine (Bipa), (R)-2-amino-3-(carboxymethylsulfanyl)propanoic acid (Bmc), 4-carboxymethoxyphenylalanine (Bmp), 4-benzoylphenylalanine (Bpa), 3-benzothienylalanine (Bta), 5H-thiazolo[3,2-a]pyridine-3-carboxylic acid (Btd), β-t-butyl-alaine (Bua), α-tert-butylglycine (Bug), 4-cyano-2-aminobutyric acid (Cab), cyclobutylalanine (Cba), cyclohexylalanine (Cha), homocyclohexylalanine (HoCha), α-cyclohexylglycine (Chg), citrulline (Cit), homocitrulline (HoCit), cyclopropylalanine (Cpa), cyclopentylglycine (Cpeg), 3-carboxymethyl-1-phenyl-1,3,8-triazaspiro[4,5]decan-4-one (Cptd), homocysteine (HoCys,), α,γ-diaminobutyric acid (Dbu), diethylglycine (Deg), 3,3-diphenyl-alanine (Dpa), di-n-propylglycine (Dpg), α,β-diaminopropionic acid (Dap), α,γ-diaminobutyric acid (Dab), 2-furyl-Alanine (Fua), homoarginine (HoArg), hydroxyproline (Hyp), O-benzyl-hydroxyproline (Hyp(Bzl)), homoleucine (HoLeu), 2-Indanylglycine (Ing), methionine sulfoxide (Met(O)), methionine methylsulfonium (Met (S-Me)), 3-(1-naphthyl)alanine (Nal1), 3-(2-naphthyl)alanine (Nal2), 3-(carboxymethylamino)propanoic acid (Nglu), nipecotic acid (Nip), isonipecotic acid (IsoNip), norleucine (Nle), norvaline (Nva), octahydroindole-2-carboxylic acid (Oic), ornithine (Orn), 2-pyridylalanine (2Pal), 3-(3-pyridyl)alanine (3 Pal), 3-(4-pyridyl)alanine (4 Pal), penicillamine (Pen), homophenylalanine (HoPhe), Nα-methyl-phenylalanine ((NMe)Phe), 2-chloro-phenylalanine (Phe(2Cl)), α-methyl-phenylalanine ((CαMe)Phe), 3,4-dimethoxy-phenylalanine (Phe(3,4-di OMe)), 4-carboxyphenylalanine (Phe(4COOH)), 4-nitrophenylalanine (Phe(4-NO$_2$)), 4-trifluoromethyl-phenylalanine (Phe(4-CF$_3$)), 4-tert-butyl-phenylalanine (Phe(4-tBu)), 3,4-dichloro-phenylalanine (Phe(3,4-diCl)), phenylglycine (Phg), (2S,5R)-5-phenyl pyrrolidine-2-carboxylic acid (Ppca), propargylglycine (Pra), homoproline (HoPro), β-homoproline (βHoPro), 2-quinoylalanine (2Qal), Nα-methylglycine (Sar), homoserine (HoSer), 3-styryl-alanine (Sta), taurine (Tau), 4-thiazoylalanine (Tha), 3-(2-thienyl)alanine (2Thi), 3-(3-thienyl)alanine (3Thi), thiazolidine-4-carboxylic acid (Thz), thiazolidine-2-carboxylic acid (Thz(2-COOH)), tetrahydro-isoquinoline-3-carboxylic acid (3Tic), (R)-1,2,3,4-tetrahydroisoquinoline-3-carboxylic acid (Tic), 3,5-dinitrotyrosine (Tyr(3,5-di NO$_2$)), 3-nitrotyrosine (Tyr (3-NO$_2$)), 3,5-diiodotyrosine (Tyr(diI)), and Nα-methyl-valine ((NMe)-Val), a phenylalanine analog, derivatives of lysine, and stereoisomers thereof (see, Liu and Lam, *Anal. Biochem.*, 295:9-16 (2001)). As such, the unnatural α-amino acids are present either as unnatural L-α-amino acids, unnatural D-α-amino acids, or combinations thereof.

The amino acids can also be categorized as basic, acidic, hydrophobic and/or polar. Some suitable basic amino acids of the invention are Lys, Arg, HoArg, Agp, Agb, Dab, Dap, Orn and stereoisomers thereof. Some suitable acidic amino acids are Asp, Glu, Aad, Bec and stereoisomers thereof. Hydrophobic amino acids include, but are not limited to, Val, Leu, Ile, Met and Phe, and stereoisomers thereof. Polar amino acids include, but are not limited to, Asn, Ser, Gln, Thr, and stereoisomers thereof.

Suitable phenylalanine analogs include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe(4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe(2,4-diCl)), 3,4-dichlorophenylalanine (Phe(3,4-diCl)), 4-benzoylphenylalanine (Bpa), 4-carboxyphenylalanine (Phe(4COOH)), 4,4'-biphenylalanine (Bip), 2,3,4,5,6-pentafluorophenylalanine (Phe(F$_5$)), 3,4,5-trifluorophenylalanine (Phe(F$_3$)), 4-chlorophenylglycine (Phg(4-Cl)), 2-chlorophenylglycine (Phg(2-Cl)), 3-chlorophenylglycine (Phg(3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr(Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and Dbu, include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. See, Table 1 for a description of the structures for each of the lysine derivatives. Derivatives of Orn and Dbu are similar to the lysine derivatives with corresponding carboxylic acid attached to the side chain of Orb and Dbu, respectively.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hey, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe(4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Amino acid mimetics are chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

N-substituted glycines are unnatural amino acids based on glycine, where an amino acid side-chain is attached to the glycine nitrogen atom. Suitable amino acid side-chains (e.g., R groups) include, but are not limited to, side chains present in naturally-occurring amino acids and side-chains present in unnatural amino acids such as amino acid analogs. Examples of N-substituted glycines suitable for use in the present invention include, without limitation, N-(2-aminoethyl)glycine, N-(3-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., *Drug Dev. Res.*, 35:20-32 (1995)). As such, peptoids containing at least one unnatural α-amino acid, D-amino acid, or a combination thereof are within the scope of the present invention.

In some embodiments, radical $X_3$ of formula (I) can be Lys, Arg, HoArg, Agp, Agb, Dab, Dap or Orn, and stereoisomers thereof. Moreover, radical $X_5$ of formula (I) can be Asp, Glu, Aad or Bec, and stereoisomers thereof. Analogues of Lys useful in the compounds of the present invention include, but are not limited to, Orn, Dab, and Dap. Analogues of Arg include, but are not limited to, HoArg, Agp, Agb, and stereoisomers thereof.

In other embodiments, radical $X_3$ can be Lys, Arg, HoArg, Agp, or Orn, and stereoisomers thereof. In addition, radical $X_5$ can be Asp, Glu, Aad or Bec, and stereoisomers thereof. In some other embodiments, radical $X_3$ can be Arg, and radical $X_5$ can be Asp. In still other embodiments, the amino acids of radicals $X_3$ and $X_5$ are each in the L-configuration.

In some embodiments, the compound can have formula (Ia):

$$X_1\text{-}X_2\text{-RGD-}X_6\text{-}X_7\text{-}X_8 \quad\quad (\text{Ia}).$$

In some other embodiments, the compound can have formula (Ib):

$$X_1\text{-GRGD-}X_6\text{-}X_7\text{-}X_3 \quad\quad (\text{Ib}).$$

The peptides of this invention are cyclized via disulfide or diselenium ring closure. Examples of amino acids suitable for cyclization of the peptides include, but are not limited to, Cys, Pen, Sec and HoCys. In general any amino acid comprising a thiol can participate in the formation of a disulfide bond. Similarly, any amino acid comprising a selenium atom can participate in the formation of a diselenium bond. Non-limiting examples of such an amino acid is selenocysteine. In some embodiments, radicals $X_1$ and $X_8$ can each independently be Cys, Pen, Sec or HoCys, and stereoisomers thereof. In some embodiments, both of radicals $X_1$ and $X_8$ are each independently Cys or Pen, and stereoisomers thereof. In some other embodiments, radicals $X_1$ and $X_8$ are each a D-amino acid. In still other embodiments, radicals $X_1$ and $X_8$ are each independently DCys or DPen. In yet other embodiments, both of radicals $X_1$ and $X_8$ are DCys.

In other embodiments, the compound can have formula Ic:

$$c\text{-}X_2\text{-RGD-}X_6\text{-}X_7\text{-}c \quad\quad (\text{Ic}).$$

In some other embodiments, the compound can have formula Id:

$$c\text{-GRGD-}X_6\text{-}X_7\text{-}c \quad\quad (\text{Id}).$$

In some other embodiments, the compound can have formula II:

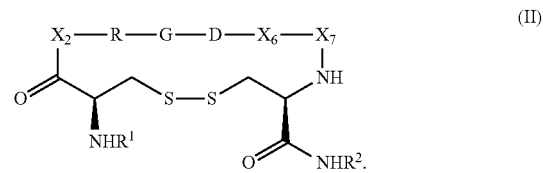

(II)

$R^1$ of formula (II) can be H, $C_{1-6}$ alkyl, —C(O)$R^{1a}$, or L-A, wherein $R^{1a}$, can be $C_{1-6}$ alkyl, $C_{1-6}$ heteroalkyl, $C_{1-6}$ alkyl-NH$_2$, $C_{1-6}$ alkyl-C(O)N(H)—$C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, or $C_{1-6}$ alkyl-heteroaryl, wherein the cycloalkyl, heterocycloalkyl, heteroaryl and aryl groups are optionally substituted with halogen, —NO$_2$, —OH, —CN, $C_{1-6}$ alkyl, $C_{1-6}$ alkoxy, $C_{1-6}$ haloalkyl and $C_{1-6}$ haloalkoxy. $R^2$ of formula (II) can be H, $C_{1-6}$ alkyl or L-A. And radical L can be a linker and radical A can be an active agent.

In still other embodiments, radicals $R^1$ and $R^2$ of formula (II) can each independently be H, $C_{1-6}$ alkyl or L-A. And radical L can be a linker and radical A can be an active agent.

In still other embodiments, $R^1$ can be acetyl, 3-amino propanoyl, Ebes, isobutyryl, valeryl, cyclohexyl acetyl, 5-bromo-2-furoyl, 3-phenyl propionyl, p-chlorophenyl acetyl, 4-nitrobezoyl, 3,5-dihydroxy beznoyl, 4-(trifluoromethyl)benzoyl, 2-Methylthiazole-4-carbonyl, nicotinyl, 2-naphthoyl, or biphenyl-4-carbonyl.

Linkers useful in the present invention includes those possessing one or more different reactive functional groups that allow for covalent attachment of moieties such as a peptide to a chelating agent. The linking moiety possesses two or more different reactive functional groups. In some cases multivalent linkers can be used and multiple RGD peptides of the invention and/or multiple active agents can be linked via the linker. Suitable linkers include, without limitation, those available from Pierce Biotechnology, Inc. (Rockford, Ill.). In preferred embodiments of the present invention, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker. Some suitable linkers include, but are not limited to, β-alanine, 2,2'-ethylenedioxy bis(ethylamine) monosuccinamide (Ebes) and bis(Ebes)-Lys. Other suitable linkers include those with biotin. Additional linkers can be found in

*Bioconjugate Techniques*, Greg T. Hermanson, Academic Press, 2d ed., 2008 (incorporated by reference in its entirety herein).

Active agents, A, can be broadly selected. In some embodiments the active agents can be selected from drugs, vaccines, aptamers, avimers scaffolds based on human A domain scaffolds, diabodies, camelids, shark IgNAR antibodies, fibronectin type III scaffolds with modified specificities, antibodies, antibody fragments, vitamins and cofactors, polysaccharides, carbohydrates, steroids, lipids, fats, proteins, peptides, polypeptides, nucleotides, oligonucleotides, polynucleotides, and nucleic acids (e.g., mRNA, tRNA, snRNA, RNAi, microRNA, DNA, cDNA, antisense constructs, ribozymes, etc, and combinations thereof). In one embodiment, the active agents can be selected from proteins, peptides, polypeptides, soluble or cell-bound, extracellular or intracellular, kinesins, molecular motors, enzymes, extracellular matrix materials and combinations thereof. In another embodiment, active agents can be selected from nucleotides, oligonucleotides, polynucleotides, and nucleic acids (e.g., mRNA, tRNA, snRNA, RNAi, DNA, cDNA, antisense constructs, ribozymes etc and combinations thereof). In another embodiment, active agents can be selected from steroids, lipids, fats and combinations thereof. For example, the active agent can bind to the extracellular matrix, such as when the active agent is hyaluronic acid. Other active agents include diagnostic or therapeutic agents, such as drugs, radiolabels, imaging agents, chemotherapy agents and nanoparticles. In some embodiments, the active agent can be biotin.

Imaging agent refers to a label that is attached to the compounds of the present invention for imaging a tumor, organ, or tissue in a subject. The imaging moiety can be covalently or non-covalently attached to the compound. Examples of imaging moieties suitable for use in the present invention include, without limitation, radionuclides, biotin, fluorophores such as fluorescein, rhodamine, Texas Red, Cy2, Cy3, Cy5 or Cy5.5, Alexa 350, Alexa 405, Alexa 488, Alexa 546, Alexa 555, Alexa 568, Alexa 594, Alexa 633, Alexa 647, Alexa 680, R-phycoerythrin, antibodies, horseradish peroxidase, alkaline phosphatase, derivatives thereof, and mixtures thereof. Exemplary methods for synthesizing the compounds of the present invention as a biotin conjugate or as a DOTA conjugate are provided in Examples 12 and 13, respectively. One skilled in the art will know of other suitable methods for conjugating a particular imaging moiety to the compounds of the present invention.

Radiolabel refers to a nuclide that exhibits radioactivity. A "nuclide" refers to a type of atom specified by its atomic number, atomic mass, and energy state, such as carbon 14 ($^{14}C$). "Radioactivity" refers to the radiation, including alpha particles, beta particles, nucleons, electrons, positrons, neutrinos, and gamma rays, emitted by a radioactive substance. Radionuclides suitable for use in the present invention include, but are not limited to, fluorine 18 ($^{18}F$), phosphorus 32 ($^{32}P$), scandium 47 ($^{47}Sc$), cobalt 55 ($^{55}Co$), copper 60 ($^{60}Cu$), copper 61 ($^{61}Cu$), copper 62 ($^{62}Cu$), copper 64 ($^{64}Cu$), copper 67 ($^{67}Cu$), gallium 66 ($^{66}Ga$), gallium 67 ($^{67}Ga$), gallium 68 ($^{68}Ga$), rubidium 82 ($^{82}Rb$), yttrium 86 ($^{86}Y$), yttrium 87 ($^{87}Y$), yttrium 90 ($^{90}Y$), strontium 89 ($^{89}Sr$), rhodium 105 ($^{105}Rh$), silver 111 ($^{111}Ag$), indium 111 ($^{111}In$), iodine 123 ($^{123}I$), iodine 124 ($^{124}I$), iodine 125 ($^{125}I$), iodine 131 ($^{131}I$), tin 117m ($^{117m}Sn$), technetium 99m ($^{99m}Tc$), promethium 149 ($^{149}Pm$), samarium 153 ($^{153}Sm$), holmium 166 ($^{166}Ho$), lutetium 177 ($^{177}Lu$), rhenium 186 ($^{186}Re$), rhenium 188 ($^{188}Re$), thallium 201 ($^{201}Tl$), astatine 211 ($^{211}At$), and bismuth 212 ($^{212}Bi$). As used herein, the "m" in $^{117m}Sn$ and $^{99m}Tc$ stands for meta state. Additionally, naturally occurring radioactive elements such as uranium, radium, and thorium, which typically represent mixtures of radioisotopes, are suitable examples of radionuclides. $^{67}Cu$, $^{131}I$, $^{177}Lu$, and $^{186}Re$ are beta- and gamma-emitting radionuclides. $^{212}Bi$ is an alpha- and beta-emitting radionuclide. $^{211}At$ is an alpha-emitting radionuclide. $^{32}P$, $^{47}Sc$, $^{89}Sr$, $^{90}Y$, $^{105}Rh$, $^{111}Ag$, $^{117m}Sn$, $^{149}Pm$, $^{153}Sm$, $^{166}Ho$, and $^{188}Re$ are examples of beta-emitting radionuclides. $^{67}Ga$, $^{111}In$, $^{99m}Tc$, and $^{201}Tl$ are examples of gamma-emitting radionuclides. $^{55}Co$, $^{60}Cu$, $^{61}Cu$, $^{62}Cu$, $^{66}Ga$, $^{68}Ga$, $^{82}Rb$, and $^{86}Y$ are examples of positron-emitting radionuclides. $^{64}Cu$ is a beta- and positron-emitting radionuclide.

Nanoparticles useful in the present invention include particles having a size ranging from 1 to 1000 nm. Nanoparticles include, but are not limited to, beads, metallic particles or can in some cases be micelles, liposomes or other vesicles, or dendrimers. Other nanoparticles include carbon nanotubes and quantum dots. Nanoparticles can be packed with diagnostic and/or therapeutic agents.

In some embodiments, radical $X_2$ of formula (II) can be Gly, Ala, Sar or β-alanine, and stereoisomers thereof. Similarly, radical $X_6$ can be Val, Leu, Ile, Met, Phe, Asn, Glu, Gln, His, Lys, Arg, Asp, Gly, Ala, Ser, Thr, Tyr, Trp, Pro, Aad, Bec, Bmc, Bmp, Phe(4COOH), Hyp, HoSer, Tha, Ahch, Actp, Akch, Tyr(diI), Trp, Thz, 2Thi, 3Thi, Cit, HoCit, Aib, Nglu, or Fua, and stereoisomers thereof. In addition, radical $X_7$ can be Val, Leu, Ile, Met, Phe, Asn, Glu, Gln, His, Lys, Arg, Asp, Gly, Ala, Ser, Thr, Tyr, Trp, Pro, Bmp, HoSer, Nglu, HoCit, Bec, Aad, Hyp, Ahch, Phe(4COOH), Akch, Aecc, Abu, Phe(3,4-diOMe), Cpa, 2Thi, 3Thi, Thz, Phg, Phe(4-NO$_2$), Nle, (NMe) Phe, Aic, Chg, Bta, Bpa, Nal2, Nal1, Tic, Ppca, Cha, Bipa, Deg, Dpg, Acpc, Bmc, Cit, Sar, Tha, Pra, Actp, Aib, Agl, Acbc, Fua, Nva, Trp, Bug, Ach, (NMe)Val, Cpeg, (CαMe) Phe, Tyr(diI), Phe(2-Cl), Bua, HoPhe, HoLeu, Sta, Ing, Phe (4-CF$_3$), Oic, Dpa, Phe(4-t-Bu), HoCha or Phe(3,4-diCl), and stereoisomers thereof. In other embodiments, each of radicals $X_2$, $X_6$ and $X_7$ can be a D-amino acid.

In other embodiments, the compound of the present invention can have formula IIa:

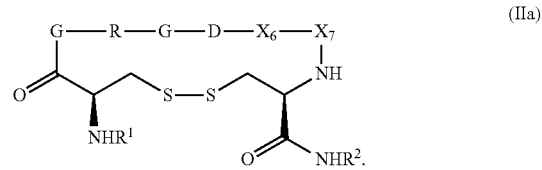

(IIa)

Radicals $R^1$ and $R^2$ of formula (IIa) are as described above. In some embodiments, radical $X_6$ can be DSer, DAsp, Ahch, Bmp, DGlu, Nglu or DCit, and radical $X_7$ can be DPhe, DGlu, DSer, DBug, DBta, DVal, DAglDPra, D(NMe)Val, D(CaMe) Val, DAbu, DIng, DIle, Actp, DTha, DAsp, DNal1 or Ppca. In some other embodiments, radical $X_6$ can be DAsp or DSer, and radical $X_7$ can be DGlu, DPhe, DSer, DVal, DBug or DBta.

In another embodiment, the compound of the present invention can be cGRGDsfc, cGRGDdfc, cGRGDsec, cGRGDdsc, cGRGDd-DBug-c, cGRGDd-DBta-c, cGRGDd-DBta-c, cGRGDdvc, CGRGDdvc, cGRGDdvC, CGRGDdvC, DPen-GRGDdv-DPen, DPen-GRGDdvc, cGRGDdv-DPen, Ac-cGRGDdvc, (β-alanine)-cGRGDdvc, (Ebes)-cGRGDdvc, caRGDdvc, c-Sar-RGDdvc, c-β-alanine-RGDdvc, cG-HoArg-GDdvc, cG-Agp-GDdvc, cG-Agp-GEdvc, cGRGDd-DAgl-c, cGRGDd-DPra-c, cGRGDd-DBug-c, cGRGDd-D(NMe)Val-c, cGRGDd-D (CaMe)Val-c, cGRGDd-DAbu-c, CGRGDd-DIng-c, c-Sar-RGD-Ahch-ic, c-Sar-RGD-Ahch-DBug-c, cGRGDd-DAgl-C, C-Sar-RGDd-DPra-C, C-Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C-Sar-RGD-Bmp-dC, CGRGDe-Ppca-c, cGRGD-Nglu-Ppca-c, cGRGDd-DNal1-c orcGRGDd-DBta-c. In other embodiments, the compound of the present invention can be cGRGDsfc, cGRGDdfc, cGRGDsec, cGRGDdsc, cGRGDdvc, cGRGDd-DBug-c or cGRGDd-DBta-c.

In another embodiment, the compound of the present invention can be cGRGDsfc, cGRGDdfc, cGRGDsec, cGRGDdsc, cGRGDdvc, CGRGDdvc, cGRGDdvC, CGRGDdvC, caRGDdvc, c-Sar-RGDdvc, c-β-alanine-RGDdvc, cGRGDd-DAgl-c, cGRGDd-DPra-c, cGRGDd-DBug-c, DPen-GRGDdv-DPen, DPen-GRGDdvc, cGRGDv-DPen, cGRGDd-D(NMe)Val-c, cGRGDd-D(CaMe)Val-c, cGRGDd-DAbu-C, CGRGDdic, CGRGDd-DIng-c, c-Sar-RGD-Ahch-ic, c-Sar-RGD-Ahch-DBug-c, cGRGDd-DAgl-C, C-Sar-RGDd-DPra-C, C-Sar-RGDd-Actp-C, c-Sar-RGDd-DPra-C, c-Sar-RGDd-Actp-C, CGRGDd-DTha-C, cGRGDd-DPra-C, cGRGDd-Actp-C, c-Sar-RGD-Ahch-iC, c-Sar-RGD-Ahch-DBug-C, C-Sar-RGD-Bmp-dC, CGRGDe-Ppca-c, CGRGD-Nglu-Ppca-c, CGRGDd-DNall-C, CGRGD-D3Thi-Ppca-c, cGRGDd-DBta-c, cG-HoArg-GDdvc, cG-(NMe)Arg-GDdvc, cGR-Sar-Ddvc, cGRG-(NMe)Asp-dvc, cG-Agp-GDdvc, cG-Agp-GEdvc, cGRGDsdC, cGRGDd-DIng-c, cGRGDd-DNal1-c, cGRGDd-DNal2-c, cGRGDd-D3Thi-c, cGRGDd-D2Thi-c, cGRGDdwc, cGRGDd-DTha-c, cGRGD-DCit-Ppca-c, cGRGDe-Ppca-c, cGRGD-NGlu-Ppca-c, cGRGD-DCit-DBta-c, cGRGD-DBec-Ahch-c, or cGRGD-DBec-DPra-c.

In other embodiments, the compound of the present invention can have formula IIb:

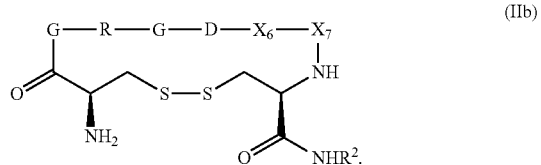

(IIb)

Radicals $X_6$ and $X_7$ of formula IIb are as defined above. Radical $R^2$ of formula IIb can be L-A. In some embodiments, radical $X_6$ of formula IIb can be DAsp, radical $X_7$ can be DVal, and radical $R^2$ can be Ebes-Ebes-Lys-biotin.

In still other embodiments, the compound can have formula IIc:

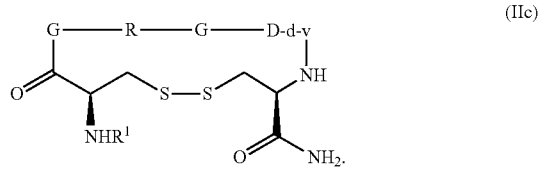

(IIc)

In other embodiments, $R^1$ of formula (IIc) is —C(O)$R^{1a}$, wherein $R^{1a}$ is as defined above.

In another embodiment, the compound of the present invention can be acetyl-cGRGDdvc, 3-amino propanoyl-cGRGDdvc, (Ebes)-cGRGDdvc, isobutyryl-cGRGDdvc, valeryl-cGRGDdvc, cyclohexyl acetyl-cGRGDdvc, 3-phenyl propionyl-cGRGDdvc, p-chlorophenyl acetyl-cGRGDdvc, 4-nitrobezoyl-cGRGDdvc, 3,5-dihydroxy beznoyl-cGRGDdvc, 4-(trifluoromethyl)benzoyl-cGRGDdvc, 2-methylthiazole-4-carbonyl-cGRGDdvc, nicotinyl-cGRGDdvc, 2-naphthoyl-cGRGDdvc, or biphenyl-4-carbonyl-cGRGDdvc.

The compounds of the present invention can be prepared by a variety of methods known to one of skill in the art. For example, the compounds can be prepared individually via known synthetic methods, such as those found in *Comprehensive Organic Transformations*, Richard C. Larock, VCH Publishers, Inc., 1989. Alternatively, the compounds can be prepared in compound libraries using the one-bead-one-compound encoding strategy described in *J. Am. Chem. Soc.* 2002, 124(26), 7678.

The one-bead one-compound (OBOC) libraries can be prepared on TentaGel S $NH_2$ resin, or any other suitable resin, using a bilayer bead encoding strategy and "split-and-mix" method. Topologically segregated bilayer beads can be generated using a biphasic solvent approach. The library compounds can be displayed on the outer layer and the coding peptide tags on the bead interior. In this manner, several libraries have been prepared. Library 1 and 2 were directly assembled on the TentaGel beads using the "split-and-mix" method. Library 3 and 4 were constructed on the outer layer of bilayer beads and the coding peptide tags are on the bead interior.

IV. Compositions

The compound of the present invention can be used in any suitable pharmaceutical compositions. In some embodiments, the present invention provides a pharmaceutical composition having a compound of formula (I) and a pharmaceutically acceptable excipient.

Pharmaceutically-acceptable excipients useful herein include any physiologically inert, pharmacologically inactive material known to one skilled in the art, which is compatible with the physical and chemical characteristics of the active ingredient selected (the compounds of this invention) for use. Pharmaceutically-acceptable excipients include, but are not limited to, polymers, resins, plasticizers, fillers, lubricants, solvents, co-solvents, buffer systems, surfactants, preservatives, sweetening agents, flavoring agents, pharmaceutical grade dyes or pigments, and viscosity agents. All or part of the pharmaceutically-acceptable excipients contained in the pharmaceutically compositions described herein are used to make dosage forms.

Many methods of administering the compounds of the invention are possible. As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a compound of the present invention for preventing or relieving one or more symptoms associated with cancer or an inflammatory or autoimmune disease. By "co-administer" it is meant that a compound of the present invention is administered at the same time, just prior to, or just after the administration of a second drug (e.g., anti-cancer agent, anti-inflammatory agent, immunosuppressive agent, etc.).

The compounds of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to affect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch.

The pharmaceutical compositions can be administered to the patient in a variety of ways, including topically, parenterally, intravenously, intradermally, intramuscularly, intranasally, via aerosol, colonically, rectally or intraperitoneally. Preferably, the pharmaceutical compositions are administered parenterally, topically, intravenously, intramuscularly or orally.

In clinical studies, number of lesions, tumor size, and tumor growth rate can be monitored by radiography, tomography, and, where possible, direct measurement of tumor mass. Anti-tumor effects can also be measured using molecular biology and biochemistry techniques, such as ELISA, PCR, western blotting, or immunocytochemistry.

The pharmaceutically effective amount of a composition required as a dose will depend on the route of administration, the type of cancer being treated, and the physical characteristics of the patient. The dose can be tailored to achieve a desired effect, but will depend on such factors as body surface area, weight, diet, concurrent medication and other factors which those skilled in the medical arts will recognize.

The foregoing are general guidelines only that can be expanded or altered based on, for example, disease type and grade, patient age, health status, and sex, the particular drugs used in combination, the route and frequency of administration, and experimental and clinical findings using a multidrug combination.

V. Methods

The compounds of the present invention can be identified by a variety of assay methods known to one of skill in the art. For example, a cell-growth-on-bead assay for screening OBOC combinatorial bead libraries to identify synthetic ligands for cell attachment and growth or proliferation of epithelial and non-epithelial cells can be used. Cells can be incubated with the library for 24 to 72-hours, allowing them to attach and grow on the beads. Those beads with cells growing are removed, and the ligand on the bead is identified. Such methods are taught by U.S. Pat. Nos. 7,262,269 and 6,670,142, which are incorporated herein by reference in their entirety.

TABLE 1

Activity of Compounds

| Compound | Sequence | MS[1] (calcd./found[M + 1]+) | IC$_{50}$ ($\mu$M)[2,3] |
|---|---|---|---|
| LXW1 | cGRGDsfc | 840.3001/841.3122 | ++ |
| LXW2 | cGRGDdfc | 868.2951/869.3029 | ++ |
| LXW3 | cGRGDsec | 822.2743/823.2816 | +++ |
| LXW4 | cGKGDsec | 794.2682/795.2777 | >20 |
| LXW5 | cGRGDdsc | 808.2587/809.2687 | ++ |
| LXW6 | cGKGDdsc | 780.2525/781.2620 | >20 |
| LXW7 | cGRGDdvc | 820.2956/821.3032 | +++ |
| LXW8 | cGKGDdvc | 792.2889/793.2970 | >20 |
| LXW9 | CGRGDdvc | 820.2956/821.4890 | ++ |
| LXW10 | cGRGDdvC | 820.2956/821.5106 | ++ |
| LXW11 | CGRGDdvC | 820.2956/821.3802 | >20 |
| LXW12 | Acetyl-cGRGDdvc | 862.3062/863.5238 | +++ |
| LXW13 | caRGDdvc | 834.3113/835.2645 | ++ |
| LXW14 | c-Sar-RGDdvc | 834.3113/835.4168 | ++ |
| LXW15 | c-β-alanine-RGDdvc | 834.3113/835.5603 | ++ |
| LWX16 | cGRGDd-DAgl-c | 818.2800/819.3598 | ++ |
| LWX17 | cGRGDd-DPra-c | 816.2643/817.4833 | ++ |
| LXW18 | cGRGDd-DBug-c | 834.3113/835.5552 | +++ |
| LXW19 | DPen-GRGDdv-DPen | 876.3582/877.6212 | ++ |
| LXW20 | DPen-GRGDdvc | 848.3269/849.3022 | ++ |
| LXW21 | cGRGDdv-DPen | 848.3269/849.3101 | ++ |
| LXW22 | cGRGDd-D(NMe)Val-c | 834.3113/835.5206 | +++ |
| LXW23 | cGRGDd-D(CaMe)Val-c | 834.3113/835.3547 | + |
| LXW25 | cGRGDd-DAbu-c | 806.2800/807.6071 | +++ |
| LXW26 | cGRGDdic | 834.3113/835.7302 | ++ |
| LXW31 | CGRGDd-DIng-c | 908.3269/909.3024 | + |
| LXW32 | c-Sar-RGD-Ahch-i c | 874.3789/875.6035 | >20 |
| LXW33 | c-Sar-RGD-Ahch-DBug-c | 874.3789/875.9000 | >20 |
| LXW34 | cGRGDd-DAgl-C | 818.2800/819.3598 | >20 |
| LXW35 | C-Sar-RGDd-DPra-C | 830.2800/831.2598 | + |
| LXW36 | C-Sar-RGDd-Actp-C | 862.3062/863.5035 | >20 |
| LXW37 | C-Sar-RGDd-DPra-C | 830.2800/831.4218 | + |
| LXY38 | c-Sar-RGDd-Actp-C | 862.3062/863.4321 | >20 |
| LXW39 | CGRGDd-DTha-C | 875.2473/876.2368 | + |
| LXW40 | cGRGDd-DPra-C | 816.2643/817.3682 | ++ |
| LXW41 | cGRGDd-Actp-C | 848.2905/849.4125 | >20 |
| LXW42 | c-Sar-RGD-Ahch-iC | 874.3789/875.5609 | >20 |
| LXW43 | c-Sar-RGD-Ahch-DBug-C | 874.3789/875.2862 | |
| LXW44 | C-Sar-RGD-Bmp-dC | 956.3117/957.4640 | >20 |
| LXW45 | CGRGDe-Ppca-c | 908.3269/909.3922 | >20 |
| LXW46 | CGRGD-Nglu-Ppca-c | 908.3269/909.5686 | >20 |
| LXW47 | CGRGDd-DNal1-C | 918.3113/919.3979 | ++ |
| LXW48 | cGRGDd-DBta-c | 924.2677/925.2214 | +++ |
| LXW51 | cG-HoArg-GDdvc | 834.3113/835.4362 | >20 |
| LXW53 | cG-(NMe)Arg-GDdvc | 834.3113/835.2916 | +++ |
| LXW54 | cGR-Sar-Ddvc | 834.3113/835.4932 | >20 |
| LXW55 | cGRG-(NMe)Asp-dvc | 834.3113/835.4901 | >20 |
| LXW56 | 3-amino propanoyl-cGRGDdvc | 891.3327/892.5297 | +++ |
| LXW57 | (Ebes)-cGRGDdvc | 1050.4223/1051.6333 | +++ |
| LXW58 | cG-Agp-GDdvc | 792.2643/793.3561 | >20 |
| LXW59 | cG-Agp-GEdvc | 806.2800/807.2740 | >20 |
| LXW62 | cGRGDsdC | 808.2582/809.8384 | + |
| LXW63 | cGRGDd-DIng-c | 908.3269/909.3024 | +++ |
| LXW64 | cGRGDd-DNal1-c | 918.3113/919.3979 | +++ |
| LXW65 | cGRGDd-DNal2-c | 918.3113/919.9768 | +++ |
| LXW66 | cGRGDd-D3Thi-c | 874.2520/875.8966 | +++ |
| LXW67 | cGRGDd-D2Thi-c | 875.2473/875.8777 | +++ |
| LXW68 | cGRGDdwc | 907.3065/908.0561 | +++ |
| LXW69 | cGRGDd-DTha-c | 875.2473/876.2499 | ++ |
| LXW70 | cGRGD-DCit-Ppca-c | 936.3694/937.3555 | + |
| LXW71 | cGRGDe-Ppca-c | 908.3269/909.3323 | ++ |

TABLE 1-continued

Activity of Compounds

| Compound | Sequence | MS[1] (calcd./found[M + 1]+) | IC$_{50}$ (μM)[2,3] |
|---|---|---|---|
| LXW72 | cGRGD-NGlu-Ppca-c | 908.3269/909.3024 | + |
| LXW73 | cGRGD-DCit-DBta-c | 966.3259/967.2925 | ++ |
| LXW74 | cGRGD-DBec-Ahch-c | 922.3095/923.2324 | |
| LXW75 | cGRGD-DBec-DPra-c | 876.2677/877.2109 | |
| LXW76 | isobutyryl-cGRGDdvc | 890.3375/891.4310 | +++ |
| LXW77 | valeryl-cGRGDdvc | 904.3531/905.4380 | ++ |
| LXW78 | cyclohexyl acetyl-cGRGDdvc | 944.3844/945.4463 | ++ |
| LXW80 | 3-phenyl propionyl-cGRGDdvc | 952.3531/953.4526 | +++ |
| LXW81 | p-chlorophenyl acetyl-cGRGDdvc | 972.2985/973.3254 | ++ |
| LXW82 | 4-nitrobezoyl-cGRGDdvc | 969.3069/970.5460 | ++ |
| LXW83 | 3,5-dihydroxy beznoyl-cGRGDdvc | 956.3117/957.3084 | +++ |
| LXW84 | biphenyl-4-carbonyl-cGRGDdvc | 1000.3531/1001.4553 | +++ |
| LXW85 | 4-(trifluoromethyl)benzonyl-cGRGDdvc | 992.3092/993.3198 | +++ |
| LXW86 | 2-Methylthiazole-4-carbonyl-cGRGDdvc | 945.2891/946.4421 | +++ |
| LXW89 | 2-naphthoyl-cGRGDdvc | 974.3375/975.2495 | +++ |
| LXW90 | 5-bromo-2-furoyl-cGRGDdvc | 992.2116/993.1967 | ++ |
| LXW92 | nicotinyl-cGRGDdvc | 925.3171/926.2625 | ++ |

[1] MS of LXW1-8 were measured by ESI-HRMS. MS of LXW9-92 were measured by MALDI-TOF.
[2] The IC$_{50}$ of LXW1-8 was tested on the inhibition of binding of FITC-Echistatin against αvβ3-K562. After identification of LXW7, the IC$_{50}$ of other peptide analogues (LXW9-92) was determined by inhibiting the binding of biotinylated LXW7 against αvβ3-K562 cells. LXW7 (IC$_{50}$ = 0.59 ± 0.06) itself was used as an internal reference for LXW9-92.
[3] +++, <1 μM; ++, 1 μM ≤ x ≤ 10 μM; +, >10 μM.

The compounds of the present invention are useful to the treatment of a variety of conditions and disease states. For example, the compounds can be used to treat conditions and disease states that are modulated by the αvβ3 integrin. The αvβ3 integrin serves as a receptor for a variety of extracellular matrix proteins displaying the arginine-glycine-aspartic acid (RGD) tripeptide sequence. These proteins include vitronectin, fibronectin, fibrinogen, laminin, collagen, Von Willibrand's factor, osteoponin, and adenovirus particles. The αvβ3 integrin, expressed on the surface of various normal and cancer cell types, is involved in multiple physiological processes including angiogenesis, apoptosis, and bone resorption. During angiogenesis, attachment of endothelial αvβ3 integrin to the extracellular matrix is required for the survival and maturation of newly forming blood vessels and ligands against αvβ3 integrin induce apoptosis of angiogenic vascular cells, leaving pre-existing quiescent blood vessels unaffected. In addition, αvβ3 integrin has been observed to be over-expressed on metastatic tumor cells such as malignant melanoma and glioblastoma. Since integrin plays a key role in angiogenesis and metastasis of human tumors, αvβ3 integrin ligands are of great interest to advances in targeted-therapy and cancer imaging.

In some embodiments, the present invention provides a method of inhibiting αvβ3 integrin, where the method involves contacting the αvβ3 integrin with an amount of a compound of the present invention sufficient to inhibit the activity of the αvβ3 integrin. In other embodiments, the contacting is conducted in an in vitro assay. In some other embodiments, the contacting is conducted in in vivo. In still other embodiments, the present invention provides a method of binding to αvβ3 integrin.

Figure 7:
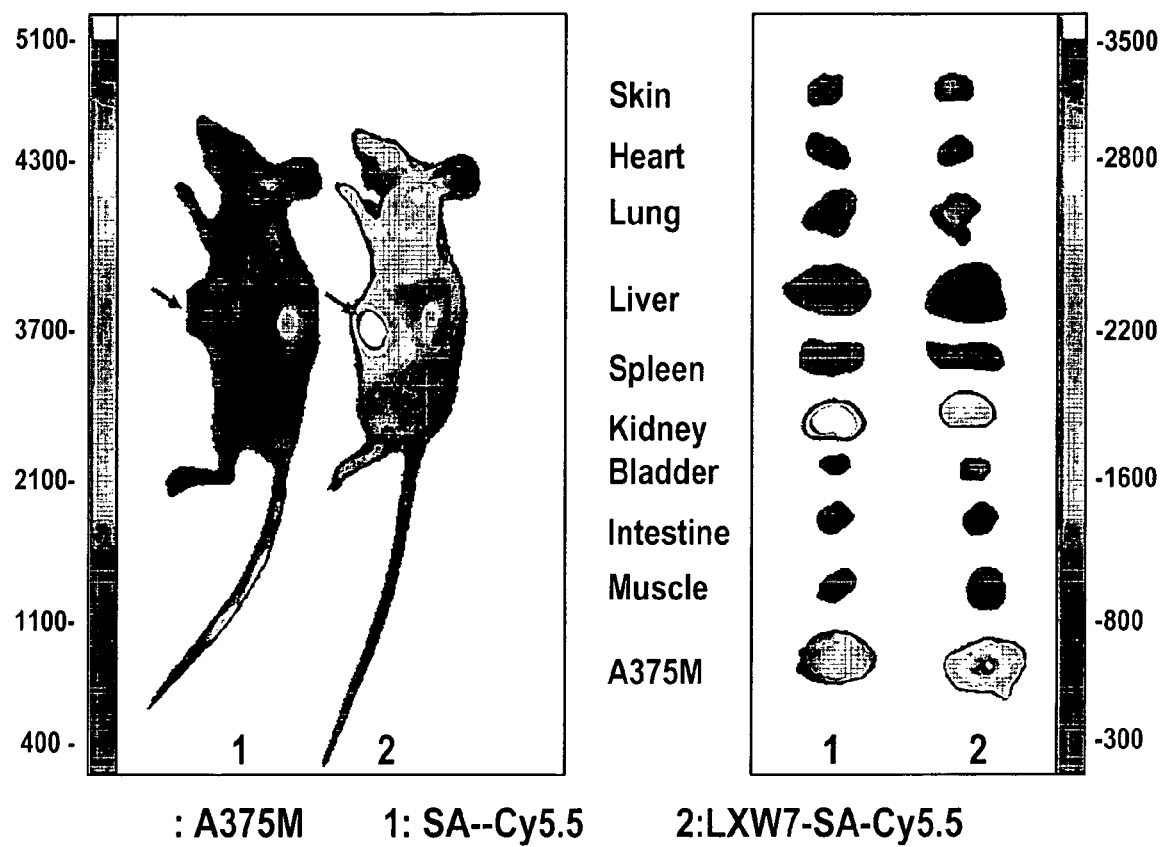
FIG. 7 shows in vivo and ex vivo near infra red fluorescent imaging on nude mice implanted with A375M xenograft 6 hrs after tail vein injection with (1) Streptavidin-Cy5.5 alone or (2) Biotinylated LXW7-Streptavidin-Cy5.5 complex. Kidney uptake was high in both mice but preferential uptake into the tumor was noted in mice given LXW7-Streptavidin-Cy5.5 complex.
Figure 8A:
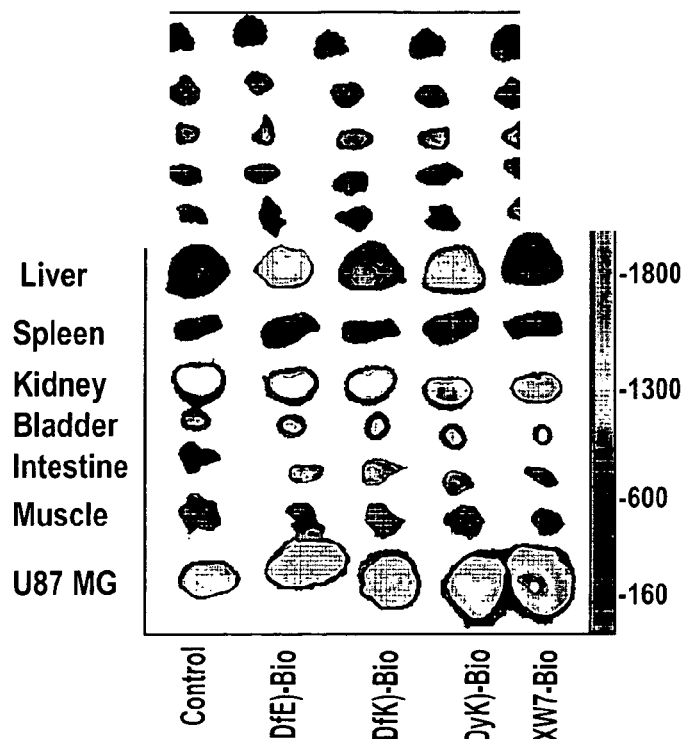
FIGS. 8a, 8b and 8c show (a) Ex vivo imaging of U-87MG xenograft bearing nude mice 6 hrs after tail vein injection with complex of Streptavidin-Cy5.5-biotinylated LXW7 and cyclic RGD pentapeptides (cyclo(RGDfE), cyclo(RGDfK) and cyclo(RGDyK). It is evident that for LXW7, tumor uptake was high, liver uptake was low. The reverse was true for the other three cyclic RGD pentapeptides. Relative fluorescence uptake by tumor and liver was quantified in (b) and (c).
Figure 8B:
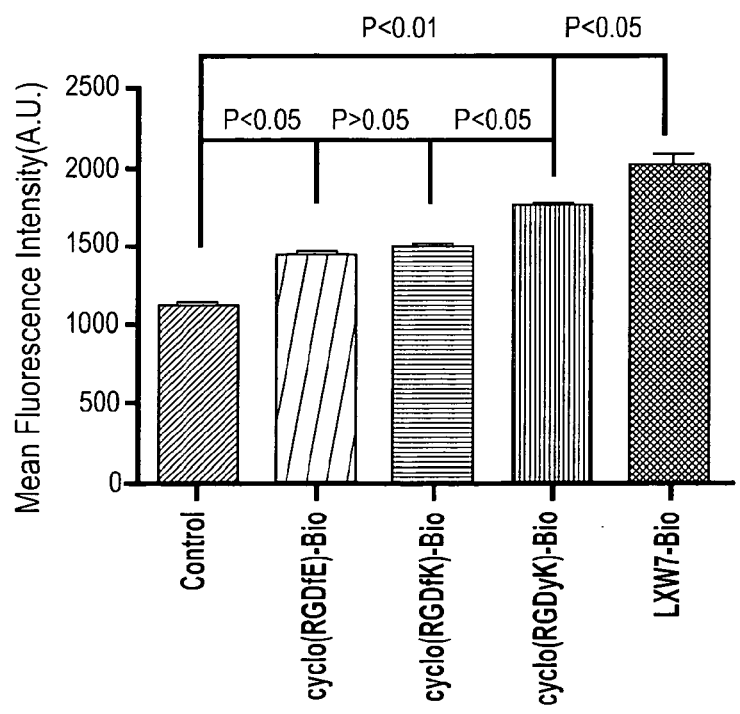
Figure 8C:
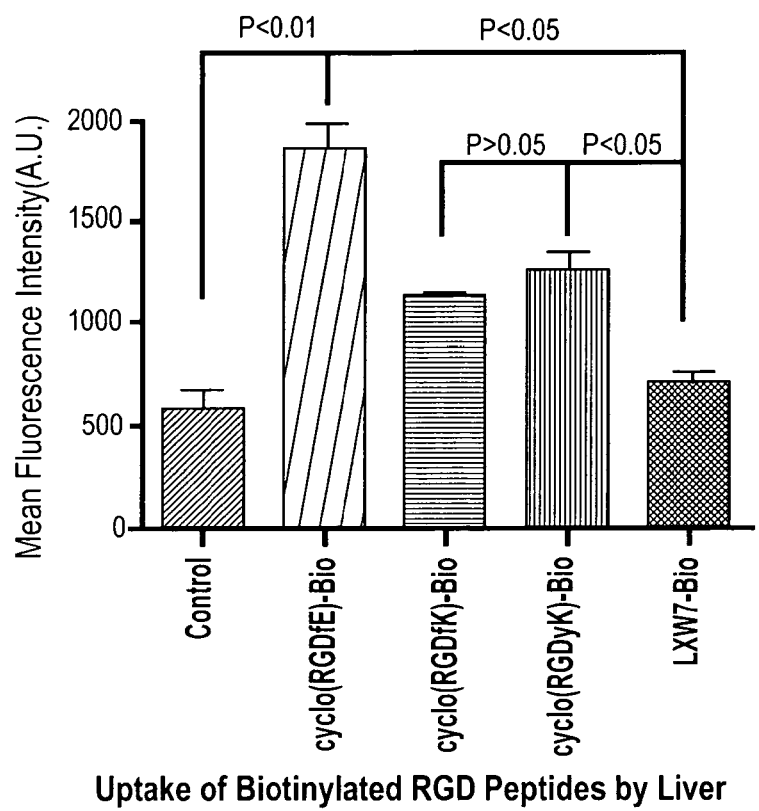
Figure 9:
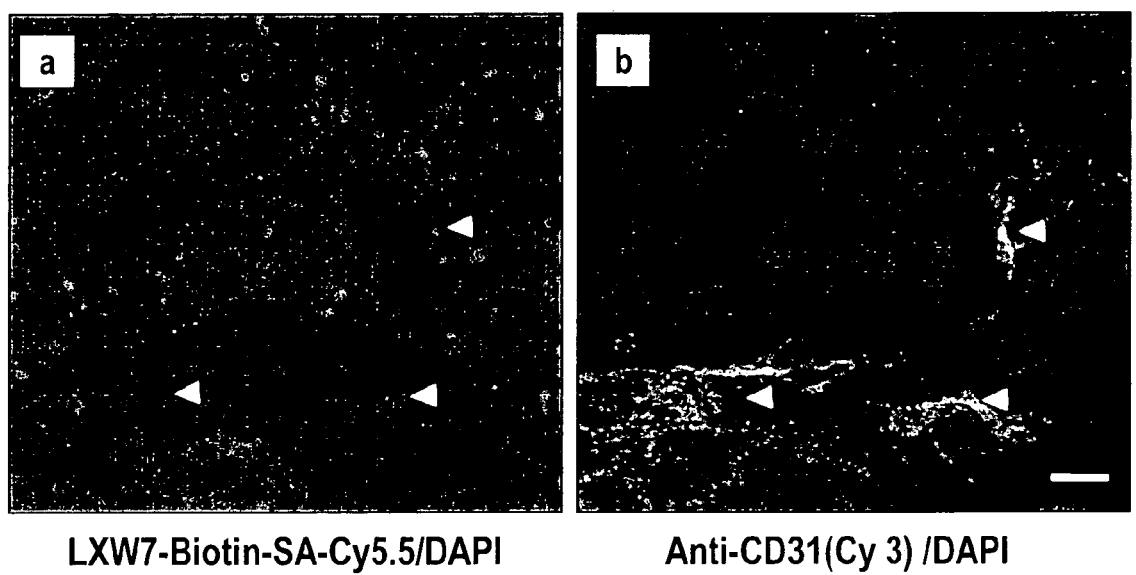
FIGS. 9a and 9b show (a) Confocal microscopy analysis of excised U-87MG xenograft after tail vein injection of nude mouse with LXW7-Biotin-SA-Cy5.5 complex. The nuclei were counter-stained with DAPI. It is evident that the Cy5.5 complex was taken up into the tumor cells cytoplasm. (b) The cryosection was also stained by anti-CD31 antibody. It appeared that imaging complex was also found at the tumor blood vessel cells (shown by white arrow head).

In other embodiments, an αvβ3 integrin receptor present on a cancer cell can be contacted with a compound of the present invention. In some other embodiments, the compounds can be linked to a radiolabel or an imaging agent and administered to a subject for diagnosis. FIGS. 7 and 8 showed non-limiting examples of such imaging. The compounds of this invention can also be linked to a chemotherapeutic and administered to a subject in need of treatment.

In some other embodiments, the present invention provides a method of treating cancer by administering to a subject in need thereof a therapeutically effective amount of a compound of the present invention. The compound of the present invention can be linked to an active agent described above in order to treat the cancer. Such chemotherapeutic conjugates can be used to treat various cancers where αvβ3 integrin is expressed, including, but not limited to, glioblastoma and melanoma. Other cancers that can be treated using the compounds and methods of the present invention include, but are not limited to, ovarian cancer, breast cancer, lung cancer, bladder cancer, thyroid cancer, liver cancer, pleural cancer, pancreatic cancer, cervical cancer, testicular cancer, colon cancer, anal cancer, bile duct cancer, gastrointestinal carcinoid tumors, esophageal cancer, gall bladder cancer, rectal cancer, appendix cancer, small intestine cancer, stomach (gastric) cancer, renal cancer, cancer of the central nervous system, skin cancer, choriocarcinomas; head and neck cancers, osteogenic sarcomas, fibrosarcoma, neuroblastoma, glioma. Non-small-cell lung cancer, Kaposi's sacrcoma, prostate cancer.

In some other embodiments, the present invention provides a method for the analysis of tumors cells for personalized medicine. For example, the compounds of the present invention can be immobilized on a solid surface in a microarray format for cell binding studies or used as a probe for flow cytometry analysis. In still other embodiments, the compounds of the present invention are useful as immobilized ligands on the scaffold for tissue engineering.

VI. Examples

Materials

TentaGel S NH2 resin (90 μm diameter) was purchased from Rapp Polymere GmbH (Tubingen, Germany). Rink amide MBHA resin (0.59 mmole/g), HOBt, Alloc-OSu and Fmoc-OSu were purchased from GL Biochem (Shanghai, China). Amino acid derivatives were purchased from Anaspec (San Jose, Calif.), Advanced ChemTech (Louisville, Ky.) and NeoMPS SA (Strasbourg, France). cyclo(RGDfE), cyclo(RGDyK) and cyclo(RGDfK) were obtained from Peptides International (Louisville, Ky.). DIC, DIPEA, phenylsilane, tetrakisphenylphosphine palladium (0), all organic solvents and other chemical reagents were purchased from Aldrich (Milwaukee, Wis.). The solvents were directly used in the library synthesis without further purification unless otherwise noted. A Perkin-Elmer/Applied Biosystems Protein Sequencer (ABI Procise 494) was used for library bead decoding. Analytical HPLC analysis were performed on a Water 2996 HPLC system equipped with a 4.6×150 mm Waters Xterra MS C18 5.0 μm column and employed a 20 min gradient from 100% aqueous H$_2$O (0.1% TFA) to 100% acetonitrile (0.1% TFA) at a flow rate of 1.0 mL/min. Preparative HPLC purification was performed on a System Gold 126NMP solvent module (Beckman) with a C18 column (Vadac, 20 mm×250 mm, 5 m, 300 Å, C18, 7.0 ml/min) 45 min gradient from 100% aqueous H$_2$O (0.1% TFA) to 100% acetonitrile (0.1% TFA), 214 nm. Mass spectra were acquired on a Thermo Fisher LTQ Orbitrap (San Jose, Calif.) fitted with an electrospray source in the positive ion mode. The molecules were measured in FT mode in the orbitrap at 100K resolution with <5 ppm mass accuracy. Loop injections were made with standard electrospray conditions using a methanol and 0.1% formic acid/water solvent system. Mass spectra were also measured on an ABI 4700 TOF/TOF (MALDI-TOF-MS) instrument. This instrument employs an Nd: Yag laser (352 nm) at a repetition rate of 200 Hz. The applied accelerating voltage was 20 kV. Spectra were recorded in delayed extraction mode (300 ns delay). All spectra were recorded in the positive reflector mode. Spectra were sums of 1000 laser shots. Matrix alpha-cyano-4-hydroxycinnamic acid was prepared as saturated solutions in 0.1% TFA in 50% $CH_3CN$.

General Methods for Library Synthesis.

Coupling completeness and Fmoc deprotection are tested by Kaiser test. For Fmoc deprotection, beads are incubated with 20% 4-methyl piperidine solution in DMF twice (5-mim, 15 min) and then thoroughly washed with DMF, MeOH and DMF three times each, respectively. For Alloc deprotection, the resulting beads were incubated with (Pd $(PPh_3)_4$) (0.2 eqiv) and $(PhSiH_3)$ (20 eqiv) in DCM for 30 min (twice), and washed with 0.5% diethyldithiocarbamic acid sodium salt in DMF (3 times) and DMF (5 times). For library synthesis, a typical synthetic cycle utilizing the "split-and-mix" approach is described as follows: (1) beads are split into aliquots as desired; (2) each aliquot of beads is coupled with a specific Fmoc-protected amino acid in the presence of HOBt and DIC for 2 h; (3) All aliquots of beads are mixed together and washed with DMF five times. Libraries 1, 2, 3 and 4 were prepared as shown in Table 2.

TABLE 2

Structures of Libraries 1, 2, 3 and 4

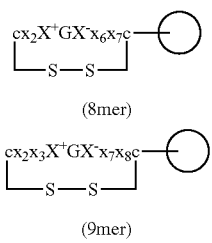

TFA-based cleavage cocktail (TFA:phenol:water:thioanisole:Tis, 10:0.5:0.5:0.5:0.25, v/w/v/v/v) for 3 h. After neutralization with 10% DIPEA/DMF (twice), the resin was washed sequentially with DMF, MeOH, DCM, DMF, DMF/water (60%, 30%) and water, three times each. Then the beads was transferred to a 1 liter bottle, to which was added 500 mL mixture of water, acetic acid and DMSO (75:5:20, pH=6). The beads were shaken for two days until the Ellman test was negative. After filtration, the beads were thoroughly washed with $H_2O$. Finally, the bead library was stored in 75% ethanol/water and ready for screening.

TABLE 3

Amino acids used in the synthesis of Library 1:

$X_1, X_6, X_7$

| No. | Amino acid | No. | Amino acid | No. | Amino acid | No. | Amino acid |
|---|---|---|---|---|---|---|---|
| 1 | DHis | 2 | DArg | 3 | DLys | 4 | DAsp |
| 5 | DGlu | 6 | DPhe | 7 | DAla | 8 | DLeu |
| 9 | DMet | 10 | DIle | 11 | DTrp | 12 | DPro |
| 13 | DVal | 14 | Gly | 15 | DGln | 16 | DAsn |
| 17 | DSer | 18 | DTyr | 19 | DThr | | |

Carboxylic acids used in the preparation of N-acyl cyclic peptides were obtained from commercially available sources.

Example 1

Preparation of 8mer Library 1

Figure 2:
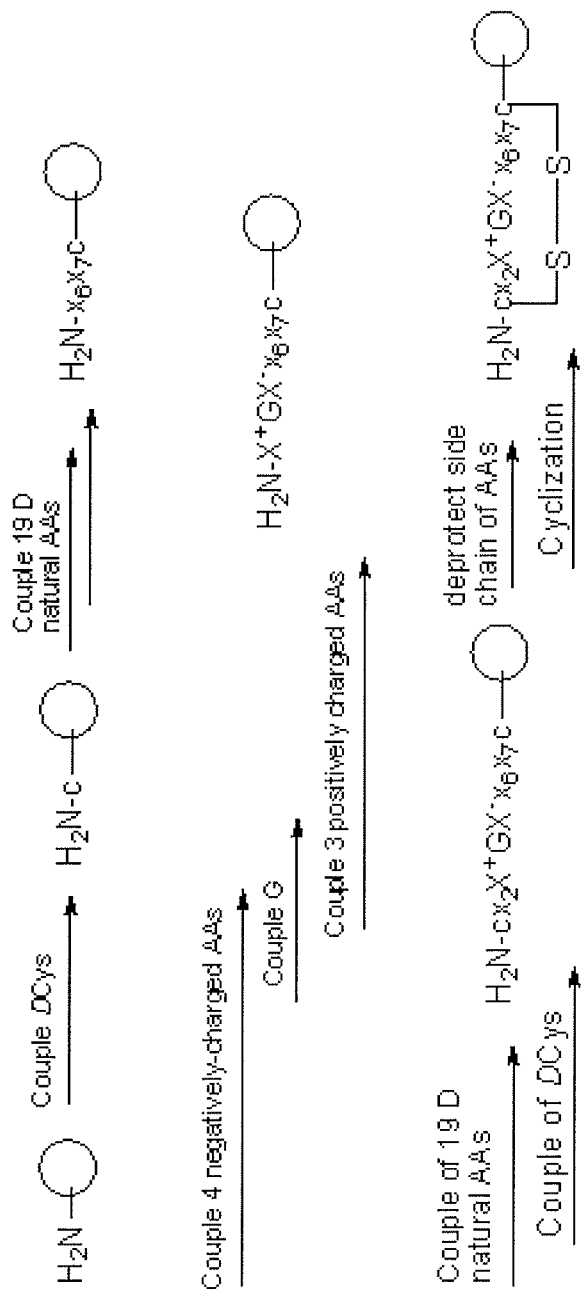
FIG. 2 shows the synthetic route for Library 1.

Library 1 was prepared according to the scheme shown in FIG. 2. TentaGel resin (2 g, loading: 0.27 mmole/g) was swollen in DMF for 4 h. After filtration, a solution of Fmoc-D-Cys(Trt)-OH (948.83 mg, 1.62 mmole), HOBt (218.7 mg, 1.62 mmole) and DIC (250.85 µL, 1.62 mmole) was added to the beads. The coupling reaction was carried out at room temperature for 2 h. After filtration, the beads were washed three times each with DMF, MeOH and DMF. The beads were subjected to Fmoc deprotection with 20% 4-methyl pieriene (5 min, 15 min). After washing with DMF, MeOH and DMF, the beads were split into 19 columns and respectively coupled with 19 natural D amino acid (See Table 3) in a similar manner described above. According to the standard "split-mix" approach, the library was completed. The beads were then dried under vacuum for overnight before adding a TABLE 3-continued Amino acids used in the synthesis of Library 1:

$X^+$

| No. | Amino acid | No. | Amino acid | No. | Amino acid |
|---|---|---|---|---|---|
| 1 | Arg | 2 | Lys | 3 | Orn |

$X^-$

| No. | Amino acid | No. | Amino acid | No. | Amino acid | No. | Amino acid |
|---|---|---|---|---|---|---|---|
| 1 | Asp | 2 | Glu | 3 | Aad | 4 | Bec |

TABLE 4

Structure of unnatural amino acids in Library 1

| Fmoc-Aad(OtBu)—OH | Fmoc-Bec(OtBu)—OH | Fmoc-Orn(Boc)—OH |
|---|---|---|
| FmocHN-CH(COOH)-CH2-CH2-C(=O)-OtBu | FmocHN-CH(COOH)-CH2-S-CH2-CH2-C(=O)-OtBu | FmocHN-CH(COOH)-CH2-CH2-CH2-NHBoc |

Example 2

Preparation of 9mer Library 2

The same synthetic route and amino acids used in the synthesis of library 1, were employed with the exception of an additional amino acid added at $x_8$ position to create a 9mer.

Example 3

Preparation of 8mer Library 3

Figure 10:
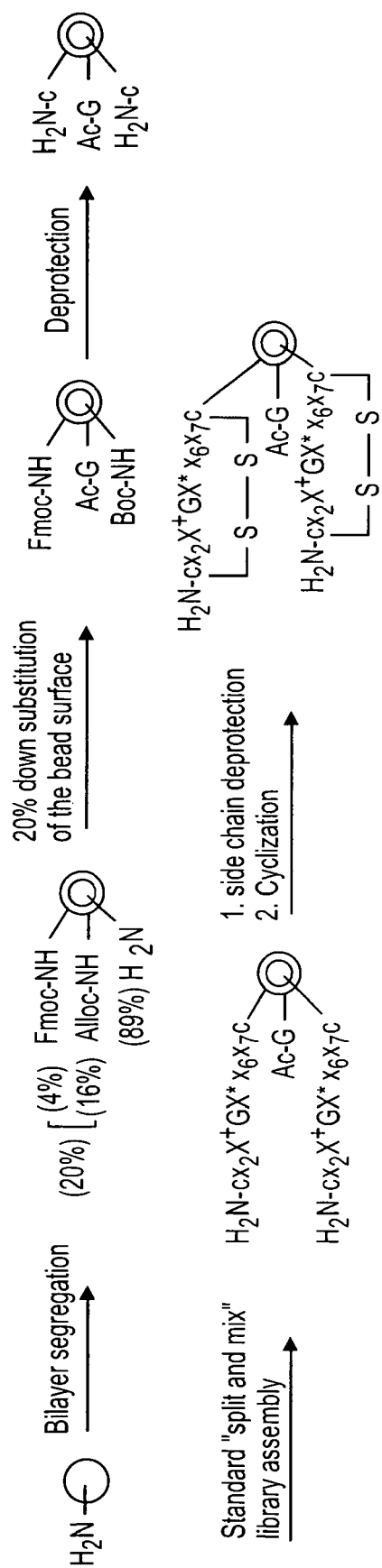
FIG. 10 shows the synthetic route of Library 3.

Library 3 was prepared according to the scheme shown in FIG. 10. TentaGel resin (2 g, loading: 0.27 mmole/g) was swollen in water for 24 h. After filtration, a solution of Fmoc-OSu (7.29 mg, 0.0216 mmole), Alloc-OSu (17.2 mg, 0.0864 mmole) and DIPEA (37.60 µL, 0.216 mmole) in DCM/diethyl ether (110 mL:90 mL) was added to the beads, and the reaction was allowed to occur under vigorously shaking for 30 min. Then the inner layer of the beads was protected by treatment with (Boc)$_2$O (589.30 mg, 2.7 mmole)/DIPEA (940.4 µL, 5.4 mmole) for 2 h. After Alloc deprotection, a solution of Ac-Gly-OH (101.12 mg, 0.864 mmole), HOBt (117 mg, 0.864 mmole) and DIC (128.3 µL, 0.864 mmole) in DMF was used to block the exposed N-terminus on the bead surface. Upon Fmoc deprotection and Boc deprotection, the library was synthesized under the same condition as library 1, following the standard "split-and-mix" approach. The beads were then dried under vacuum overnight before adding a TFA-based cleavage cocktail (TFA:phenol:water:thioanisole:Tis, 10:0.5:0.5:0.5:0.25, v/w/v/v/v) for 3 h. After neutralization with 10% DIPEA/DMF (twice), the resin was washed sequentially with DMF, MeOH, DCM, MeOH, DMF, DMF/water (60%/30%) and water, three times each. The beads were then transferred to a 1 liter bottle, and a 500 mL mixture of water, acetic acid, and DMSO (75:5:20, pH=6) was added. The beads were shaken for two days until the Ellman test was negative. After filtration, the beads were thoroughly washed with H$_2$O. Finally, the bead library was stored in 75% ethanol/water and ready for screening.

Example 4

Preparation of Library 4

The same synthetic route and amino acids have been used as in the synthesis of library 3. However, at $X^k$ position only, Foc-Lys(Boc)-OH and Fmoc-Orn(Boc)-OH had been used as building blocks for library synthesis.

Example 5

Synthesis of Nα-9-Fluorenylmethyloxycarbonyl-lysine allyl ester (Fmoc-Lys-OAll)

The procedure as discussed in "Letters in Peptide Science 2003. 10: p. 119-125" was followed. HPLC ($t_R$=17 min, 95% purify), ESI-HRMS calcd. 408.2044, found [M+1]$^+$ 409.2120, 1H NMR (DMSO-d6, 500 MHz): δ 7.90 (d, J=7.0 Hz, 2H), δ7.78 (d, NH), δ 7.71 (t, J=5.0 Hz, 4H), δ7.42 (d, J=10 Hz, 2H), δ7.33 (d, J=5.0 Hz, 2H), δ7.9 (d, J=5.0 Hz, 2H), δ5.85-5.92 (m, 1H), δ5.30 (d, J=20 Hz, 1H), δ5.20 (d, J=10 Hz, 1H), δ4.58 (d, J=5 Hz, 2H), δ 4.34-4.37 (dd, 1H), δ4.29 (dd, 1H), δ 4.23(q, J=5 Hz, 1H), 4.04 (m, 1H), 2.77 (s, 2H), 1.63-1.72 (m, 2H), 1.51-1.56 (m, 2H), 1.34-1.37 (m, 2H)

Example 6

Synthesis of LXW7 cyclo(cGRGDdvc)

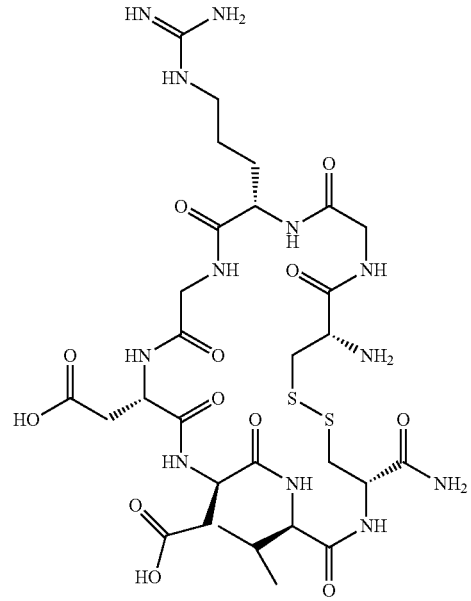 [SMILES: CC(C)[C@H]1NC(=O)[C@@H](CC(=O)O)NC(=O)[C@H](CC(=O)O)NC(=O)CNC(=O)[C@H](CCCNC(=N)N)NC(=O)CNC(=O)[C@H](N)CSSC[C@H](C(N)=O)NC1=O]

Rink amide MBHA resin (0.30 g, loading: 0.59 mmol/g) was swollen in DMF for 4 h. After filtration and Fmoc deprotection, a solution of Fmoc-D-Cys(Trt)-OH (310.42 mg, 0.53 mmol), HOBt (71.6 mg, 0.53 mmol) and DIC (78.57 µL, 0.53 mmol) was added to the beads. The coupling reaction was carried out at room temperature for 2 h. After filtration, the beads were washed three times each with DMF, MeOH, and DMF. After Fmoc deprotection, Fmoc-D-Val-OH, Fmoc-D-Asp(OtBu)-OH, Fmoc-Asp(OtBu)-OH, Fmoc-Gly-OH, Fmoc-Arg(Pbf)-OH, Fmoc-Gly-OH, and Fmoc-D-Cys(Trt)-OH were respectively coupled to the resin in the manner described above. After removal of Fmoc, the beads were sequentially washed with DMF, MeOH, DMF, DCM, and then dried under vacuum.

To the dried resin was added 5 mL of the cleavage mixture (94% TFA:2.5% water:2.5% EDT:1% TIS), and the reaction was conducted at room temperature for 2 h. The cleavage solution was then collected, concentrated, precipitated with cold diethyl ether and lyophilized. The crude peptides (200 mg) were dissolved in 200 mL of 50 mM $NH_4HCO_3$ buffer, followed by the addition of 200 mg activated charcoal. The solution was stirred at room temperature until the Ellman test was negative. The reaction solution was filtered, collected and lyophilized. The crude product was analyzed by analytical HPLC, purified by RP-HPLC (99% purity) and characterized by ESI-HRMS (Calcd. 820.2951, found $[M+1]^+$: 821.3032).

Example 7

Synthesis of Analogues

LXW7 analogues (LXW1-92) have been synthesized in a similar manner described above for LXW7, with N-capped analogues also using the procedure below.

N-capped analoges are prepared as follows: following the procedure for LXW7 above, and prior to cleavage from the beads, the beads were split into 15 portions evenly. The solution of a suitable carboxylic acid (10 equiv. 1.18 mmol), HOBt (10 equiv., 1.18 mmol) and DIC (10 equiv., 1.18 mmol) in DMF was added to the beads. The coupling reaction was carried out at room temperature overnight. The beads were washed with DMF, MeOH, DMF, DCM, and then dried under vacuum. To the dried resin was added 5 mL of the cleavage mixture (94% TFA:2.5% water:2.5% EDT:1% TIS), and the reaction was conducted at room temperature for 2 h. The cleavage solution was then collected, concentrated, precipitated with cold diethyl ether and lyophilized. The crude peptides were dissolved in 50 mM $NH_4HCO_3$ buffer (1 mg crude peptide/mL buffer), followed by the addition of activated charcoal. The solution was stirred at room temperature until the Ellman test was negative. The reaction solution was filtered, collected and lyophilized. The crude product was analyzed by analytical HPLC, purified by RP-HPLC and characterized by MALDI-TOF.

Example 8

Synthesis of Biotinylated Cyclo(RGDfE)

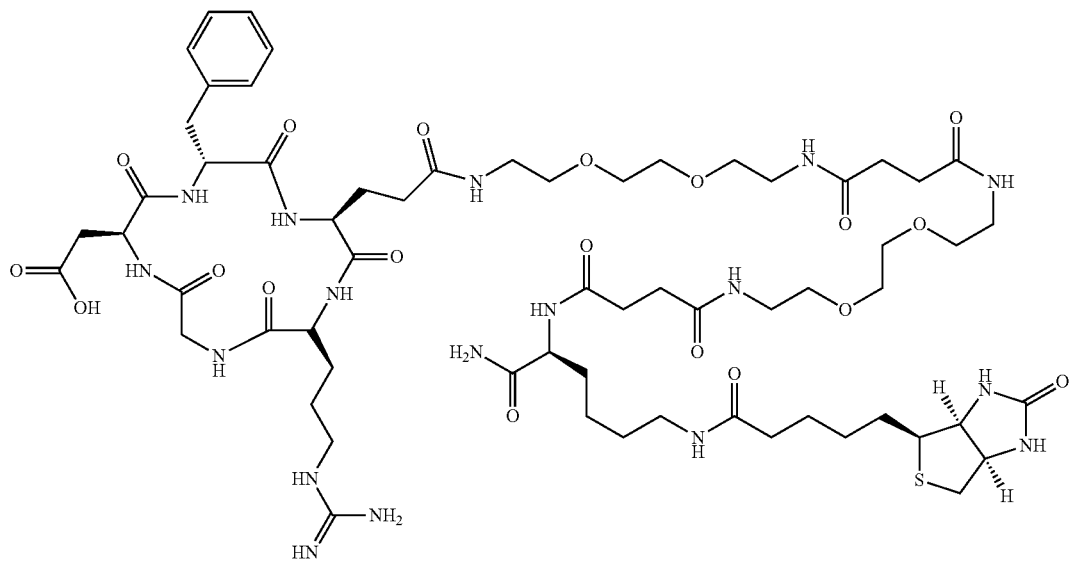

Rink amide MBHA resin (0.30 g, loading: 0.59 mmol/g) was swollen in DMF for 4 hours prior to Fmoc-deprotection. Fmoc-Lys(Alloc)-OH (240 mg, 0.53 mmol) was dissolved in a solution of HOBt (71.56 mg, 0.53 mmol) and DIC (82.07 µL, 0.53 mmol) in DMF and added into the beads. The coupling was carried out at room temperature for 2 h. After filtration, the beads were washed with DMF five times, followed by Fmocdeprotection. The beads were then subjected to two cycles of coupling of an Fmoc-Ebes linker. After Alloc deprotection, a solution of biotin (129.5 mg, 0.53 mmol), HOBt (71.56 mg, 0.53 mmol) and DIC (82.07 µL, 0.53 mmol) in DMF was added to the beads. The reaction was carried out at room temperature overnight. After Fmoc deprotection, a solution of Fmoc-Glu-OAll (216.9 mg, 0.53 mmol), HOBt (71.56 mg, 0.53 mmol) and DIC (82.07 µL, 0.53 mmol) in DMF, was added to the beads. The coupling was carried out at room temperature for 2 hours. After filtration, the beads were washed with DMF, MeOH, and DCM for 3 times, respectively. A Shorter Fmoc deprotection reaction time (3 min each time, twice) has been adopted hereafter to prevent the formation of aspartimide as a by-product. After washing with DMF, MeOH, and DMF, the beads were subjected to additional coupling and deprotection cycles stepwise with Fmoc-D-Phe-OH, Fmoc-Asp(OtBu)-OH, Fmoc-Gly-OH, and Fmoc-Arg(Pbf)-OH in the same manner described above. After removal of Fmoc, 50 mg of beads were split out and dried under vacuum. 1 ml of cleavage mixture (95% TFA:2.5% water:2.5% TIS) was added to the aliquot, and the reaction was carried out at room temperature for 2 h. The crude product was precipitated with cold diethyl ether, analyzed by RP-HPLC (major peak $t_R$=10.18 min), and characterized by ESIMS calcd: MS1475.74, found [M+1]$^+$1477.50. The small cleavage indicated that major product is ally group protected linear peptide. After Fmoc deprotection and Allyl deprotection, a solution of HATU (216.24 mg, 0.53 mmol), HOAt (72.14 mg, 0.53 mmol) and DIPEA (184.99 µL, 1.06 mmol) was added to the resin. The cyclization step was finished after two hours. After washing with DMF and DCM, the resin was dried under vacuum overnight. 5 mL of the cleavage mixture (95% TFA:2.5% water:2.5% TIS), was added to the dried resin, and the reaction was carried out at room temperature for 2 h. The liquid was then collected and concentrated. The crude product was precipitated with cold diethyl ether. The crude peptide was analyzed and purified by RP-HPLC (99% purity) and characterized by ESI-HRMS (Calcd. 1417.7024, found [M+1]$^+$: 1418.7087).

Example 9

Synthesis of Biotinylated Cyclo(RGDfK) and Cyclo(RGDyK)

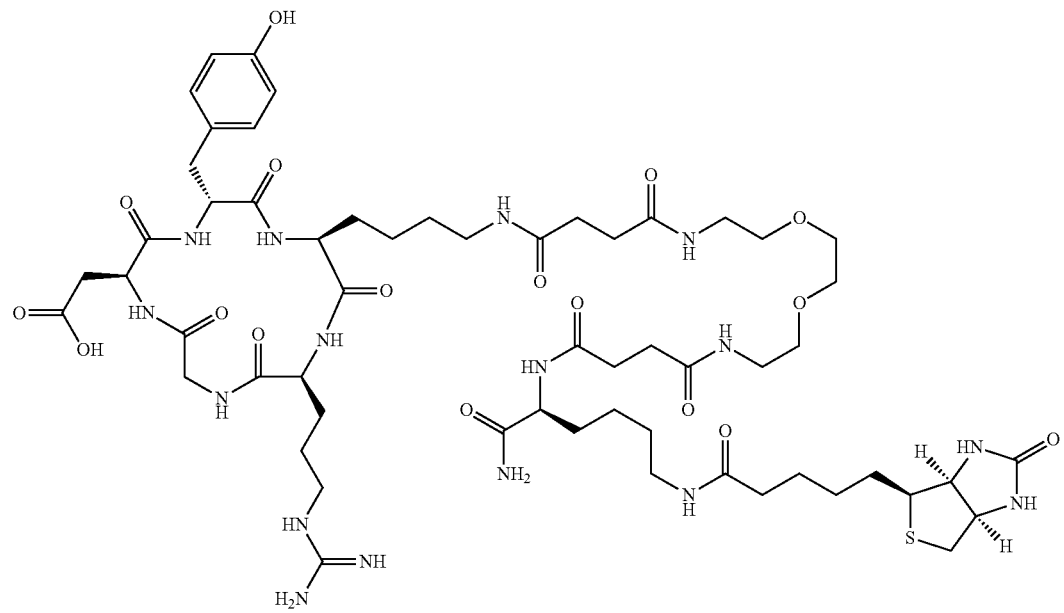

Structure of biotinylated cyclo (RGDyK)

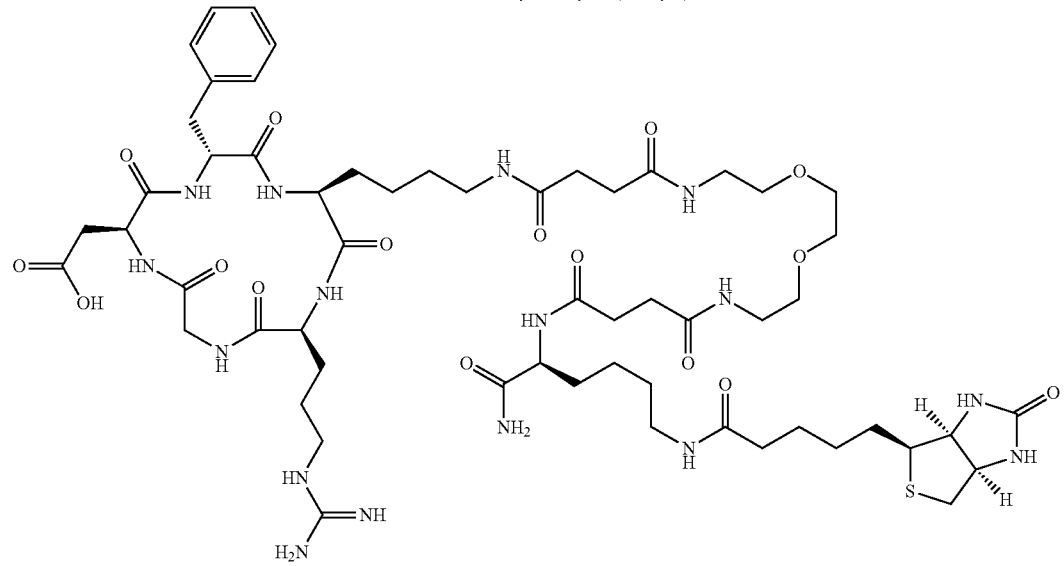

Structure of biotinylated cyclo (RGDfK)

Rink amide MBHA resin (0.30 g, loading: 0.59 mmol/g) was swollen in DMF for 4 hours prior to Fmoc deprotection with 20% 4-methyl piperidine in DMF. Fmoc-Lys(Alloc)-OH (240 mg, 0.53 mmol) was dissolved in a solution of HOBt (71.56 mg, 0.53 mmol) and DIC (82.07 µL, 0.53 mmol) in DMF and added into the beads. The coupling was carried out at room temperature for 2 h. After filtration, the beads were-washed with DMF five times, followed by Fmoc deprotection. The beads were then subjected to one cycle of coupling of an Fmoc-Ebes linker (249.84 mg, 0.53 mmol). After Alloc deprotection, a solution of biotin (129.5 mg, 0.53 mmol), HOBt (71.56 mg, 0.53 mmol) and DIC (82.07 μL, 0.53 mmol) in DMF was added to the beads. The reaction was carried out at room temperature overnight. After removal of Fmoc, the beads were then treated with succinic anhydride (177.12 mg, 1.77 mmol) and DIPEA (616.64 μL, 3.54 mmol) for 30 min at room temperature. A solution of Fmoc-Lys-OAll (216.24 mg, 0.53 mmol) in $CH_2Cl_2$-DMF (1:1) was added to the resin, followed by DIPEA (184.99 μL, 1.06 mmol), solid HATU (216.24 mg, 0.53 mmol) and HOAt (72.14 mg, 0.53 mmol). After 30 min, the resin was washed with DMF, DCM and DMF. After Fmoc deprotection, the beads were subjected to additional coupling and Fmoc deprotection cycles stepwise with Fmoc-D-Phe-OH, Fmoc-Asp(OtBu)-OH, Fmoc-Gly-OH, and Fmoc-Arg(Pbf)-OH. After Fmoc deprotection and Allyl deprotection, the head-to-tail cyclization was accomplished using HATU (201.94 mg, 0.531 mmol)/HOAt (72.3 mg, 0.531 mmol)/DIPEA (184.64 μL1, 1.06 mmol) in DMF after 2 hours. The beads were washed with DMF and DCM and dried under vacuum. To the dried resin, 5 mL of cleavage mixture (95% TFA:2.5% water:2.5% TIS) was added, and the reaction was carried out at room temperature for 2 h. The liquid was then collected and concentrated. The crude product was precipitated with cold diethyl ether. The crude peptide was analyzed and purified by RP-HPLC (purity 99%) and characterized by ESI-HRMS, calcud: 1286.6441, found [M+1]$^+$: 1287.6522).

The same procedure was adopted to synthesize cyclo (RGDyK). The resultant product was analyzed and purified by RP-HPLC and further characterized by ESI-HRMS, calcd: 1302.6391, found [M+1]$^+$: 1303.6467).

Example 10

Synthesis of Biotinylated Cyclo(cGRGDdvc)

Rink amide MBHA resin (0.30 g, loading: 0.59 mmol/g) was swollen in DMF for 4 hours prior to Fmoc deprotection with 20% 4-methyl piperidine in DMF. Fmoc-Lys(Alloc)-OH (240 mg, 0.53 mmol) was dissolved in a solution of HOBt (71.56 mg, 0.53 mmol) and DIC (82.07 μL, 0.53 mmol) in DMF and added into the beads. The coupling was carried out at room temperature for 2 h. After filtration, the beads were washed with DMF five times, followed by Fmoc deprotection. The beads were then subjected to two cycles of coupling of an Fmoc-linker (249.84 mg, 0.53 mmol). After Alloc deprotection, a solution of biotin (129.5 mg, 0.53 mmol), HOBt (71.56 mg, 0.53 mmol) and DIC (82.07 μl, 0.53 mmol) in DMF was added to the beads. The reaction was carried out at room temperature overnight. After Fmoc deprotection, Fmoc-D-Cys(Trt)-OH (310.42 mg, 0.53 mmol) was dissolved in a solution of HOBt (71.56 mg, 0.53 mmol) and DIC (82.07 μl, 0.53 mmol) in DMF and added to the beads for synthesis. The coupling was carried out at room temperature for 2 hours. After filtration, the beads were washed with DMF, MeOH, and DMF 3 times each. After Fmoc deprotection, the beads were subjected to additional coupling and deprotection cycles stepwise with Fmoc-D-Val-OH, Fmoc-D-Asp(OtBu)-OH, Fmoc-Asp(OtBu)-OH, Fmoc-Gly-OH and Fmoc-Arg (Pbf)-OH, Fmoc-Gly-OH and Fmoc-D-Cys(Trt)-OH in a similar manner described above. After removal of Fmoc, the beads were sequentially washed and dried under vacuum. To the dried resin, 5 ml of the cleavage mixture (95% TFA:2.5% water:2.5% Tis) was added and allowed to removed side chain protecting groups over a 2 h reaction at room temperature. The cleavage solution was then collected, concentrated, precipitated with cold diethyl ether and lyophilized. The crude peptides (200 mg) were dissolved in 200 ml of 50 mM $NH_4HCO_3$ buffer followed by the addition of 200 mg activated charcoal. The solution was stirred at room temperature until the Ellman test was negative. The reaction solution was filtered, collected, and lyophilized. The crude product was analyzed by analytical HPLC, purified by preparative HPLC

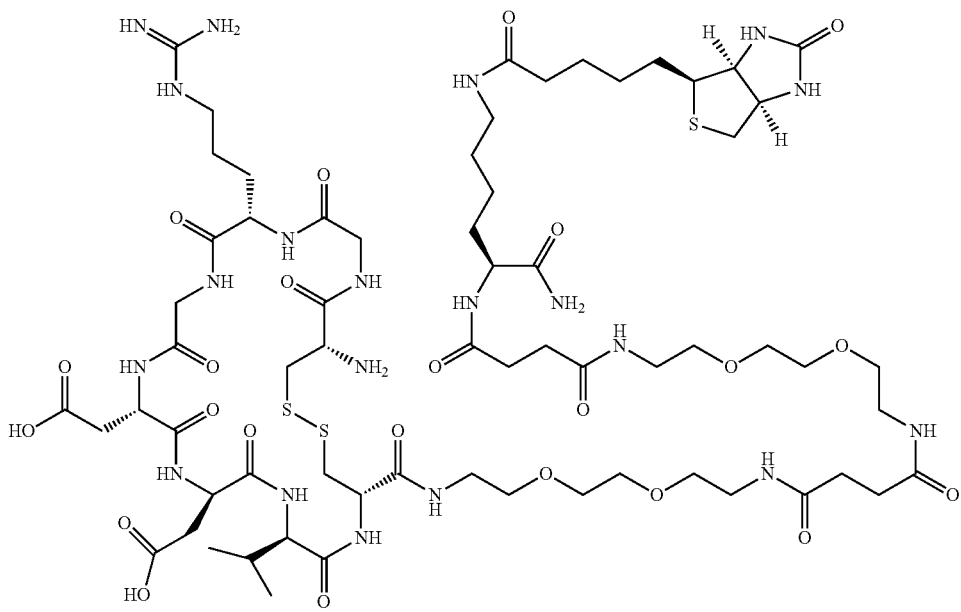 [SMILES: CC(C)[C@H]1NC(=O)[C@@H](CC(=O)O)NC(=O)[C@H](CC(=O)O)NC(=O)CNC(=O)[C@H](CCCNC(=N)N)NC(=O)CNC(=O)[C@H](N)CSSC[C@H](C(=O)NCCOCCOCCNC(=O)CCC(=O)NCCOCCOCCNC(=O)CCC(=O)N[C@@H](CCCCNC(=O)CCCC[C@@H]2SC[C@@H]3NC(=O)N[C@@H]32)C(N)=O)NC1=O]

(purity: 99%) and characterized by ESI-HRMS, calcd. 1634.7215, found [M+1]$^+$: 1635.7264).

Example 11

Integrin Binding Assay

Cells.

K562, U-87MG, and A375M were obtained from American Type Culture Colletion (Manassas, Va.). The HUVECs (human umbilical vein endothelial cells) were purchased from PromoCell company (Heidelberg, Germany). The series of α1, α2, α3, α4, α6, α9 and αvβ3 transfected K562 cells were furnished by Dr. Yoshikazu Takada in the Dermatology Department of UC Davis Medical Center. αIIbβ3-K562 was a gift donated from Dr. Jennifer Cochran (Stanford University) and Dr. Scott D. Blystone (SUNY Upstate Medical University).

Whole Cell Binding Assay and Bead Screening.

Adherent HUVECs were trypsinized with 0.05% trypsin-EDTA and neutralized with growth medium, then spun down. Suspension cells such as K562, αvβ3-K562 cells were directly collected, spun down. Cell pellet was resuspended with 10 ml growth medium in a 10 cm Petri dish. Then library beads were washed sequentially with ethanol, water, and PBS. Thereafter the beads were incubated with suspended cells, and the whole dish was kept shaking at a speed of 40 rpm inside an incubator at 37° C. under 5% CO2. The plate was then examined under an inverted microscope every 15 min. For the beads screening, at least 200 μL settled down library beads (~150,000) were screened against one cell line. Usually 100-200 beads showing strong binding were picked up, washed with 8M Guanidine Chloride, water and PBS sequentially, followed by incubation with cells again, from which 10-20 beads with relative stronger binding capacity were picked up and sent to sequence.

Flow Cytometry.

For the determination of half maximum binding inhibition concentration ($IC_{50}$) of LXW1-8, peptides at different concentrations were premixed with 2 μM FITC-Echistatin, then incubated with 3×10^5 αvβ3-K562 and K562 cells separately in 100 μl PBS containing 10% FBS and 1 mM $MnCl_2$ for 30 min on ice, followed by examination with Flow Cytometry. In this assay, there was a background binding from FITC-Echistatin to K562 cells. However, all the tested peptides had no inhibition effect to the background binding. So K562 cells incubated with 2 μM FITC-Echistatin was always used as a background reference and the mean fluorescence intensity (MFI) of this sample was subtracted from those of all the samples of αvβ3-K562 cells when the final $IC_{50}$es were calculated.

For the determination of half maximum binding inhibition concentration ($IC_{50}$) of all the LXW7 peptide analogues, peptides at different concentrations were premixed with 0.1 μM biotinylated LXW7, incubated with 3×10^5 αvβ3-K562 in 100 μl binding buffer (1×PBS containing 10% FBS and 1 mM $MnCl_2$) for 30 min on ice. The samples were washed with 1 ml washing buffer (1×PBS containing 1% FBS) one time and incubated with 1:500 dilution of streptavidin-PE (1 mg/mL) for 30 min on ice. After one additional wash, samples were tested by Flow Cytometry. The apparent $IC_{50}$ were calculated using Graph Prism software (≤www.graphpad.com≥).

Generally, the cells staining with LXW7-Bio detected by Flow Cytometry was conducted with the same procedure as following: LXW7-Bio was incubated with 3×10^5 cells on ice for 30 mM in the PBS containing 10% FBS and 1 mM $MnCl_2$, then the samples were washed with 1 ml PBS containing 1% FBS for three times, followed by incubation with 1:500 dilution of streptavidin-PE (1 mg/mL) for 30 min on ice. After one time wash, samples were tested. When the Kds of LXW7-Bio against αvβ3-K562, U-87MG and A375M were determined, total binding of different concentrations of LXW7-Bio against those cells were calculated. At the same time, another set of samples with 100 μM LXW7 in each sample besides LXW7-Bio to compete the binding from LXW7-Bio were used to determine the nonspecific binding. Then the specific binding equaled to substraction of nonspecific binding from total binding and Kds were analyzed.

To test the expression of αvβ3 integrin on U-87MG and A753M, samples were stained with 1 μg mouse anti-human αvβ3-PE (23C6, Santa Cruz Biotechnology, INC) on ice for 30 min, then washed one time and tested. For the blocking experiment, 10 μg anti-human αvβ3 (LM609, Chemicon) were premixed with 1 μM LXW7-Bio then incubated with cells, followed by streptavidin-PE detection.

The samples were analyzed with Coulter XL-MCL flow cytometry. The histogram and mean fluorescence intensity (MFI) were determined. The apparent Kd, $IC_{50}$ were calculated using Graph Prism software (≤www.graphpad.com≥).

Screening of RGD-Containing OBOC Libraries Against αvβ3 Integrin.

HUVEC cells (human umbilical vein endothelial cells) were used as a neovasculature cell model (Skovseth, D. K., et al. Methods Mol Biol, 2007. 360: p. 253-68) to identify peptide ligands against newly-formed tumor blood vessels. Two cyclic RGD containing libraries, octamer library 1 (Table 5, shown below) and nonamer library 2 (Table 2), were synthesized and screened against HUVEC cells using a whole cell binding assay (Lam, K. S., et al. Nature, 1991. 354(6348): p. 82-4). Library 1 and library 2 were designed based on the RGD motif: "X$^+$" position involves three basic L-amino acids: Lys, Arg and Orn; and "X$^-$" position includes four acidic L-amino acids: Asp, Glu, Aad and Bec. $X_2$, $X_6$, $X_7$ and $X_8$ positions were diversified with 19 D-amino acids (excluding D-cysteine). Two D-cysteines were each placed at N- and C-terminus for disulfide bond formation to cyclize the peptides. D-amino acids were chosen for multiple positions so that the resulting cyclic peptides would be resistant to proteolysis. Library 1 elicited stronger binding with HUVEC cells than Library 2, and was therefore used for further screening analysis. As shown in Table 5, RGD was found to be the preferred motif for HUVEC cells binding with Library 1.

Cells with high level of αvβ3 integrin expression would be a more appropriate cell model to be used as probe for the identification of ligands that bind specifically to neovasculature. αvβ3 integrin transfected K562 leukemia cells, expressing a high level of αvβ3 integrin and a baseline level of α5β1 integrin (expressed by the parent line), were used as a living cell probe to screen Library 1 (FIG. 1). This experiment yielded Gly as the preferred amino acid in the $X_2$ position (60%) and DAspoccurred with increased frequency (40%) in $X_6$ position. As a control, Library 1 was also screened with the parent line (non-transfected K562 cells), which yielded a higher frequency of DLys and DArg (57%) at the $X_2$ position. To further explore the amino acid preferences flanking the RGD motif, Library 3, with 20% down-substitution on bead surface to facilitate an expected higher screening stringency, was synthesized and screened with αvβ3-K562 cells. To synthesize this library, topologically segregated bilayer beads with outer layer:inner core ratio of 20:80 were generated. 80% of the outer layer was then blocked with acetylated glycine leaving only 20% of the outer layer for library compound construction. Under this higher stringency screening condition, 100% of the peptides from Library 3 yielded Gly at $X_2$ position with an acidic amino acid DAsp or DGlu at either position $X_6$ (40%) or $X_7$ (20%). Polar amino acids DAsn, DGln and DThr were also found to predominant at $X_6$ position (40%). The cGRGDdvc sequence occurred twice. Other than the 20% acidic residues, there was no obvious preference in the $X_7$ position.

The results showed that the LXW7 had the highest binding affinity to $\alpha v\beta 3$ integrin with $IC_{50}$ at $0.68\pm0.08$ μM. LXW3 showed similar affinity. The binding affinities of LXW1, LXW2 and LXW5 were found to be 2-4 times lower than that of LXW7. Changing of L-Arg to L-Lys in the "X" position in LXW4, LXW6 and LXW8 decreased the affinity. These findings validated the rationale for the Library 4 design.

TABLE 5

Peptide sequence selected from the library beads screening with cells.

| Library 1 [a] | | | Library 3 [a] | Library 4 [a] |
|---|---|---|---|---|
| | | | (4%) $cx_2X^+GX^-x_6x_7c$ —S—S— | (4%) $cx_2X^KGX^-x_6x_7c$ —S—S— |
| | | | (16%) Ac—G— | (16%) Ac—G— |
| $cx_2X^+GX^-x_6x_7c$ —S—S— | | | (80%) $cx_2X^+GX^-x_6x_7c$ —S—S— | (80%) $cx_2X^KGX^-x_6x_7c$ —S—S— |
| HUVEC | K562($\alpha 5\beta 1$) | $\alpha v\beta 3$-K562 | $\alpha v\beta 3$-K562 | $\alpha v\beta 3$-K562 |
| ckRGDdnc | crRGDqnc | cGRGDyhc | cGRGDdvc (2) [b] | cGKGDdsc(2) [b] |
| ckRGDdyc | crRGDmnc | cGRGDsfc | cGRGDdfc | cGKGDdvc |
| ckRGDric | ckRGDfqc | cGRGDmec | cGRGDdnc | cGKGDdqc |
| ckRGDyqc | ckRGDfdc | cGRGDqic | cGRGDdic | cGKGDeyc |
| crRGDdac | cmRGDhmc | cGRGDehc | cGRGDehc | cGKGDefc |
| crRGDdwc | cmRGDhdc | cGRGDdfc | cGRGDfvc | ctKGDdyc |
| caRGDhac | cqRGDymc | ckRGDdic | cGRGDetc | cGKGDsec(2) [b] |
| caRGDhmc | | ctRGDdfc | cGRGDnpc | cGKGDnyc |
| caRGDrdc | | caRGDdgc | cGRGDnyc | cGKGDnwc |
| cGRGDlgc | | cqRGDyfc | cGRGDnhc | |
| cGRGDnic | | | cGRGDnec | |
| csRGDfdc | | | cGRGDhdc | |
| csRGDqgc | | | cGRGDhgc | |
| cyRGDyec | | | cGRGDhpc | |
| cIRGDqgc | | | cGRGDqdc | |
| cpRGDwnc | | | cGRGDtyc | |
| cqRGDwpc | | | | |
| cdRGDhgc | | | | |

[a] Library 1 (8mer) was synthesized on TentaGel beads using "split-mix" strategy. Library 3 and 4 were generated in topological segregated bilayer beads, in which 80% of the outer layer (16% of total loading) is blocked by acetylated glycine; then the library is constructed on the rest of 20% of the outer layer (4% of total loading). The building blocks on different positions are $X^+$, R, K and Orn; $X^-$, Asp, Glu, Aad and Bec; $X^K$, K and Orn; $x_2$, $x_6$, and $x_7$, 19 D-amino acids (excluding D-cysteine).
[b] The number in the parenthesis indicates the appearance frequency of the peptide sequence.

To further narrow down the amino acid preferences in the $X_6$ and $X_7$ positions, we designed and synthesized Library 4, in which at "$X^K$" position, only Lys and Orn were used as building blocks. We believe excluding Arg in this position will decrease the binding contribution from the RGD motif and therefore increase the screening stringency on the $x_2$, $x_6$ and $x_7$ positions. The screening results showed that Gly was still preferred in $x_2$, and acidic amino acid (D-Asp and D-Glu) appeared with higher frequency (63%) at $x_6$ position, and more polar (including acidic residues) and hydrophobic amino acids occurred in the $x_7$ position. Interestingly, the sequence cGKGDdvc was found as expected and two other sequences, cGKGDsec and cGKGDdsc appeared twice independently.

In summary, through screening disulfide cyclized RGD containing peptide libraries against $\alpha v\beta 3$ integrin, it is shown that the RGD motif is still the preferred binding motif and the amino acids lateral to RGD showed a coordinated trend in which Gly was constantly found to be at the amino side of R and amino acids with acidic (such as DAsp and DGlu) and polar amino acids (such as DSer and DAsn) occurred with higher frequency in the $x_6$ position. Polar and hydrophobic amino acids seemed to predominant in the $x_7$ position. Following these finding, several peptides were selected for further binding affinity study (Table 1).

Binding Affinity of Leading Peptides.

Based on the screening results shown above, LXW1-8 peptides were selected for further binding affinity analysis.

TABLE 6

The equilibrium binding of LXW7 against tumor cells with $\alpha v\beta 3$ integrin expression.

| Cell Type | Kd (nM) | Bmax (A.U) |
|---|---|---|
| $\alpha v\beta 3$-K562 | 76 ± 10 | 1394 ± 57 |
| A375M | 89 ± 8 | 71 ± 4 |
| U-87 MG | 72 ± 15 | 86 ± 4 |

Binding Characterization of LXW7 and Biotinylated LXW7.

Figure 3:
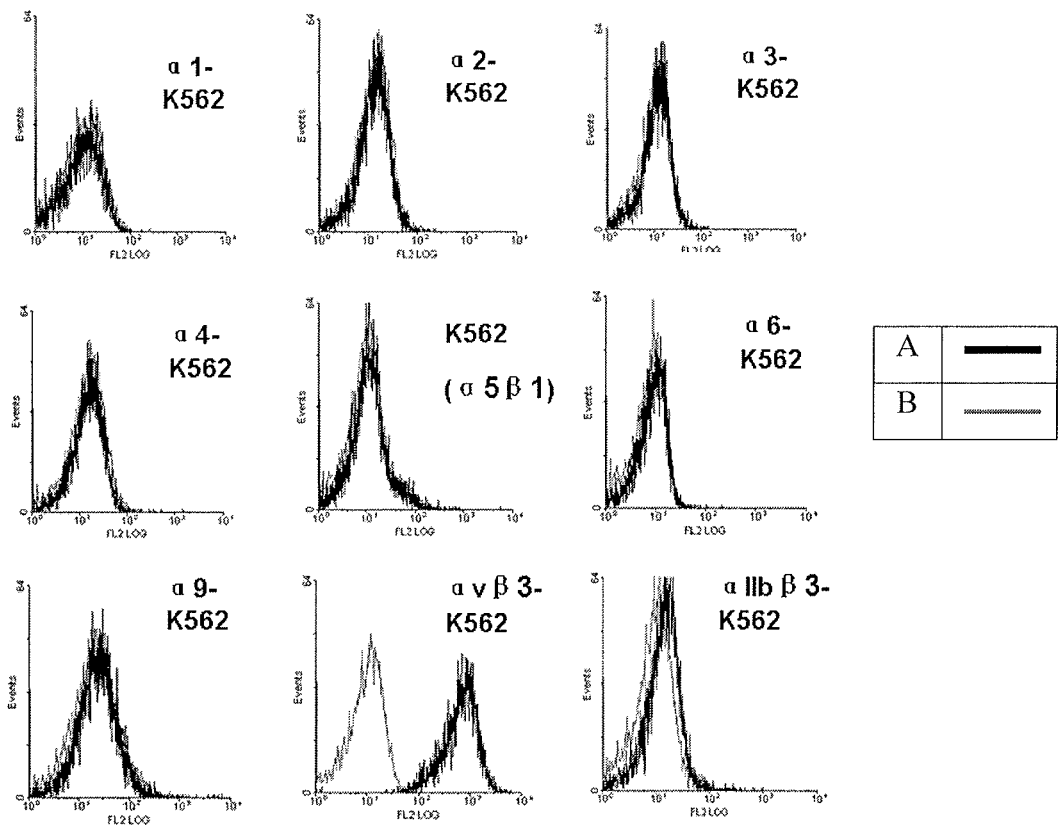
FIGS. 3a and 3b show a series of integrin transfected K562 cells stained with compounds of the present invention.
Figure 3:
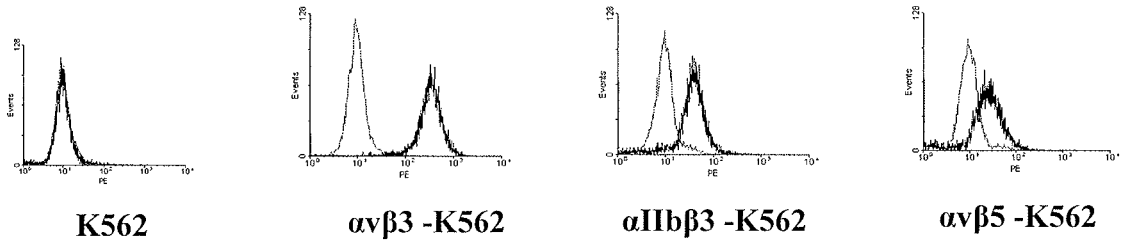
Figure 4:
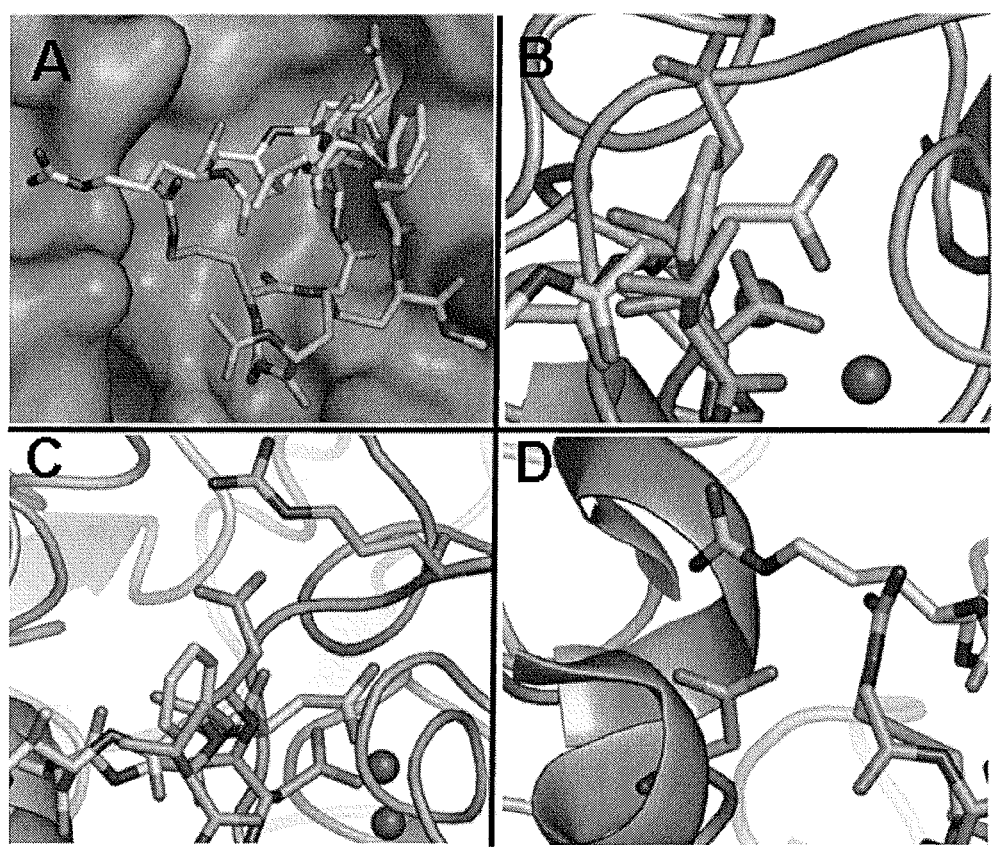
FIG. 4 shows docking simulation study on LXW7. Panel A shows the docked conformation of cyclo(RGDfV) and LXW7 on the surface of αvβ3 integrin. Panel B shows the interaction between the carboxylate side chain of Asp of the two ligands with the $Mg^{2+}$ within the MIDAS domain of the β-subunit. The salt bridge formed by the DAspfollowing the RGD in LXW7 with Arg214 in the β-subunit is shown in Panel C. Panel D shows the salt bridge formed by the Arg from the ligands with Asp218 of the α-subunit. The guanidinium side chain from the cyclo(RGDfV) is able to interact with both carboxylate oxygens while the side chain from LXW7 interacts with only one of the carboxylate oxygens.
Figure 5:
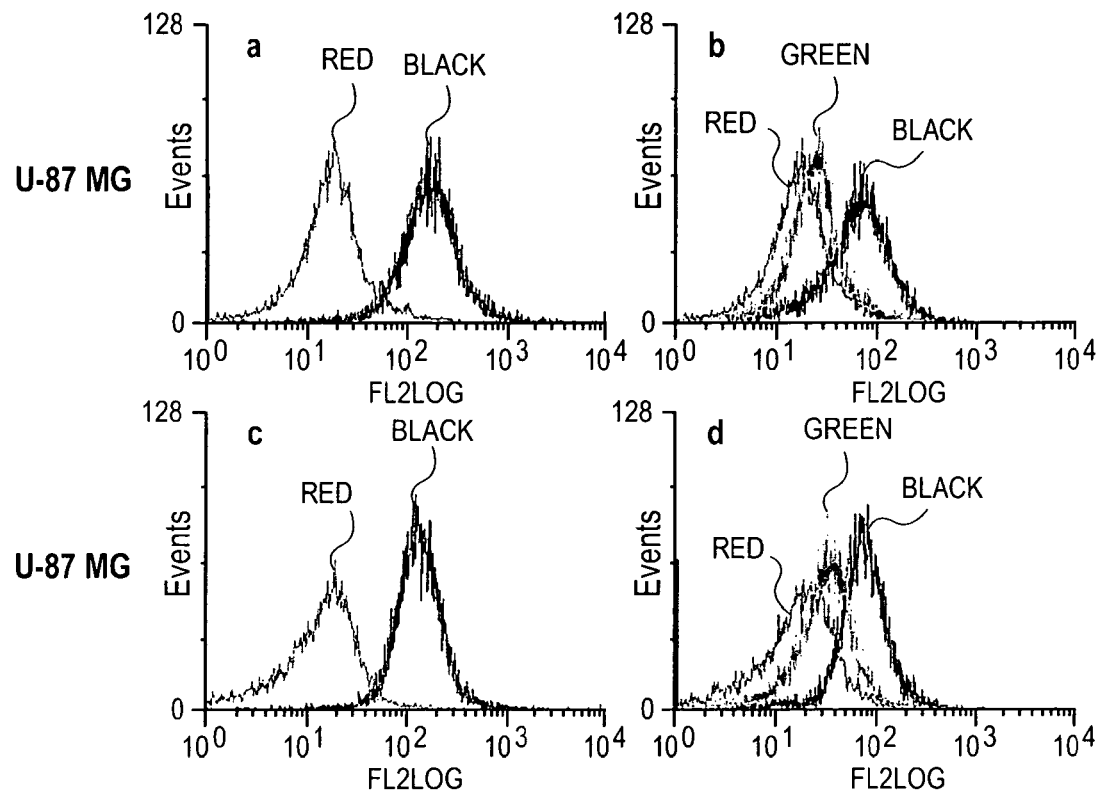
FIG. 5 shows the binding of LXW7 to U-87 MG and A375M cells was blocked by anti-αvβ3 antibody (LM609). Both glioblastoma U-87 MG (a) and melanoma A375M (c) displayed expression of αvβ3 integrin. LXW7 bound with both tumor cells, and the binding was markedly blocked by anti-human αvβ3 antibody (b,d).
Figure 6:
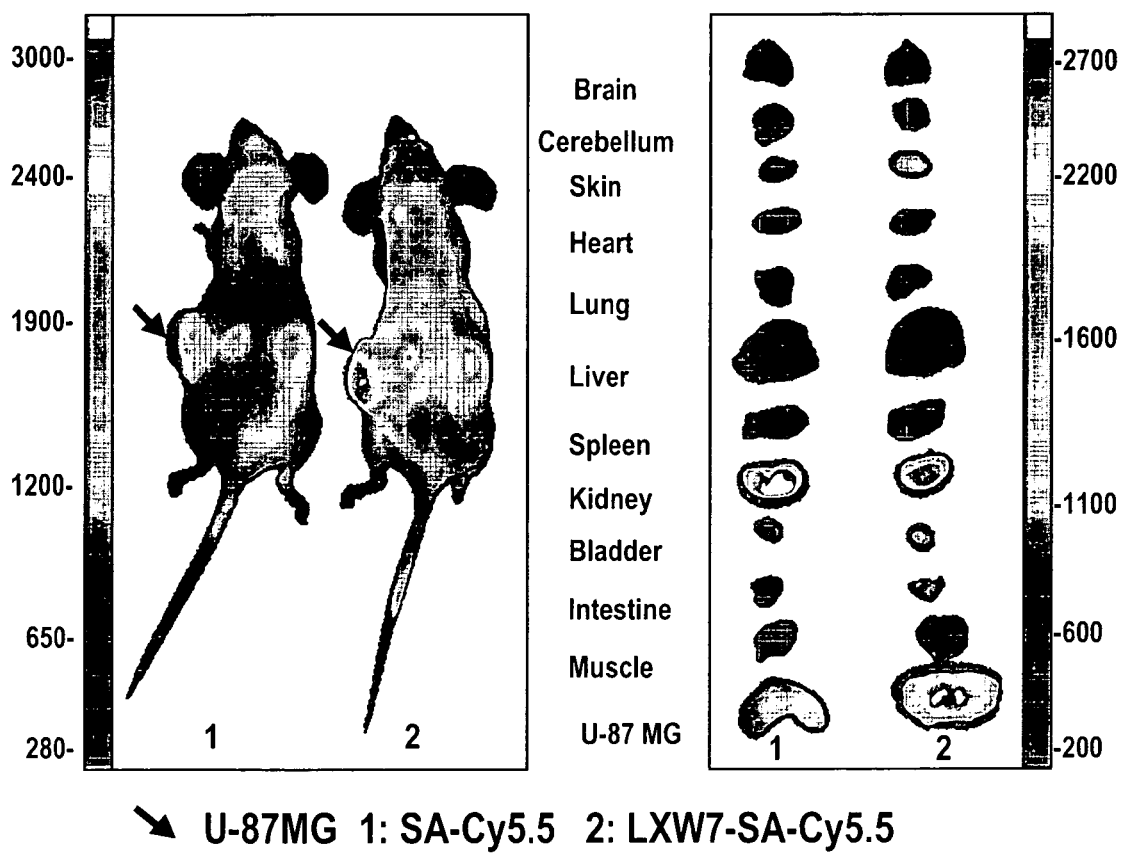
FIG. 6 shows in vivo and ex vivo near infra red fluorescent imaging on nude mice implanted with U-87 MG xenograft 6 hrs after tail vein injection with (1) Streptavidin-Cy5.5 alone or (2) Biotinylated LXW7-Streptavidin-Cy5.5 complex. Kidney uptake was high in both mice but preferential uptake into the tumor was noted in mice given LXW7-Streptavidin-Cy5.5 complex.

To test the specificity of LXW7, LXW7 was prepared in biotinylated form and incubated with $\alpha 1$, $\alpha 2$, $\alpha 3$, $\alpha 4$, $\alpha 6$, $\alpha 9$, $\alpha IIb\beta 3$ and $\alpha v\beta 3$ transfected K562 and parent K562 cells ($\alpha 5\beta 1$), followed by incubation with streptavidin-PE. The peptide binding was tested by flow cytometry and the results showed that LXW7 strongly bound to $\alpha v\beta 3$ integrin, weakly to $\alpha IIb\beta 3$ integrin, but not at all to $\alpha 1$, $\alpha 2$, $\alpha 3$, $\alpha 5$, $\alpha 6$, $\alpha 9$ integrins (FIG. 3). The binding affinities of LXW7 and these cyclic RGD pentapeptides against $\alpha v\beta 3$ integrin were compared based on their ability to inhibit FITC-Echistatin binding with $\alpha v\beta 3$-K562.

TABLE 7

Inhibition of FITC-Echistatin binding to αvβ3 transfected K562 cells by biotinylated and non-biotinylated RGD peptides. (Biotinylation negatively affects the binding affinity of head-to-tail cyclic RGD pentapeptides to αvβ3 integrin)

| Peptides | $IC_{50}$ (μM) Inhibit FITC-Echistatin binding with αvβ3-K562 | Biotinylated Peptides | $IC_{50}$ (μM) Inhibit FITC-Echistatin binding with αvβ3-K562 |
|---|---|---|---|
| cyclo(RGDfE) | 0.60 ± 0.07 | cyclo (RGDfE)-Bio | 4.7 ± 0.8 |
| cyclo (RGDfK) | 0.65 ± 0.08 | cyclo (RGDfK)-Bio | 1.37 ± 0.2 |
| cyclo (RGDfV) | 0.54 ± 0.05 | N/A | |
| cyclo (RGDyK) | 0.34 ± 0.04 | cyclo (RGDyK)-Bio | 1.35 ± 0.09 |
| cyclo (RGDf-N(Me)V-) | 0.27 ± 0.03 | N/A | |
| LXW7 | 0.68 ± 0.08 | LXW7-Bio | 0.62 ± 0.07 |

To use these cyclic peptides as drug delivery vehicles, one will need to tether these ligands to the payload such as drug-loaded liposomes, drug-loaded micelles or a radiometal chelates. For ease of testing, we biotinylated the ligands, mixed each of these biotinylated ligands with streptavidin-Cy5.5 in a 4:1 molar ratio, and then performed in vivo and ex vivo optical imaging studies.

Since LXW7 was discovered through screening OBOC combinatorial libraries with an on-bead binding assay, LXW7 already has a build-in handle at the C-terminus to which the library compound was linked to the bead. Biotinylation can be conveniently carried out at this site. In contrast, the well-studied head-to-tail cyclo(RGDf-(NMe)V-) or cyclo(RGDfV) peptides lack a handle. Consequently, many investigators replace Val with either Lys or Glu, to which the payload can be covalently linked. However, such linker can potentially affect the binding of the ligand to the integrin. We prepared cyclo(RGDyK), cyclo(RGDfK) and cyclo(RGDfE) with a biotin attached to either the Lys or Glu residues via a hydrophilic linker. We then determined the binding affinity of each of these biotinylated forms and compared them with the corresponding non-biotinylated forms. Not unexpected, LXW7 and biotinylated LXW7 were found to have near identical binding strength to αvβ3 integrin. However, biotinylation of cyclo(RGDfE), cyclo(RGDfK) and cyclo(RGDyK) resulted a 2-8 fold decrease in affinity (Table 7).

Example 12

Tumor Xenografts In Vivo and Ex Vivo Optical Imaging Studies

Animal studies were performed according to a protocol approved by IACUC of the University of California, Davis. Female athymic nude mice (nu/nu), obtained from Harlan (Indianapolis, Ind.) at 5-6 weeks of age, were injected subcutaneously in the right flank with 5×10^6 U-87MG glioblastoma cells or A375M melanoma cells suspended in 200 μl PBS. When the subcutaneous tumors reached 0.5 to 1.0 cm in diameter or 21-28 days later, the tumor-bearing mice were subjected to in vivo and ex vivo imaging studies.

Tetravalent Peptide-biotin-streptavidin complex (1.8 nmole), prepared by mixing 7.2 nmole of biotinylated peptide with 1.8 nmole of streptavidin-Cy5.5 in PBS overnight at 4° C., was injected via the tail vein in the mouse anesthetized by injection of 30 μL Nembutal (50 mg/ml) before imaging. Animals were placed on a sheet of transparency in different position. Images were acquired with a Kodak IS2000 mM Image station (Rochester, N.Y.) with excitation filter 625/20 band pass, emission filter 700 WA/35 band pass, and 150 W quartz halogen lamp light source set to maximum. Images were captured with a CCD camera set at F stop=0, FOV=150, and FP=0. Six hours post injection of imaging complex, the mice were conducted in vivo imaging, then were sacrificed and organs were excised for ex vivo imaging. Data were collected and analyzed using the Kodak ID 3.6 software by drawing the region of interest (ROI) on the image.

Example 13

Microsopic Analysis of Xenografts after Conjugate Application

Tumors were frozen and cryosectioned into sections 10 μM thick and fixed them with cold acetone for histological analysis. To detect the expression of CD31 (a marker for the vascular endothelium) in tumors, we rehydrated slides in PBS for 5 min and then blocked them in 5% BSA in PBS for 1 h at room temperature (25° C.). Slides were incubated with primary antibodies at 2-10 μg ml$^{-1}$ for 1 h at room temperature. Slides were washed three times in PBS and then added mounting solution with DAPI (Invitrogen), finally mounted them with coverslips. The slides were examined with a confocal microscope (Olympus FV-1000). The rat monoclonal primary antibody to mouse CD31 (Chemicon International) was used. The secondary antibody used was goat anti-rat IgG-Cy3 (Chemicon International).

Mean fluorescence intensities of the tumor and of the normal organ area by means of the region-of-interest function using Kodak 1D Image Analysis Software (Kodak). All the data are shown as mean+/−s.d. of n independent measurements. Student's t-test was used for statistical analysis of ex vivo imaging intensity. Statistical significance was indicated by P<0.05 and P<0.001.

Example 14

Preparation of Library 5 and 6

Following the procedure above for Library 3, a library of cyclic RGD peptides of formula Ia:

$$X_1\text{-}X_2\text{-}RGD\text{-}X_6\text{-}X_7\text{-}X_8 \tag{Ia}$$

was prepared using the following amino acids:

| POSITION | AMINO ACIDS |
|---|---|
| $X_1$ & $X_8$ | Cys, DCys |
| $X_2$ | Gly, Sar |
| $X_6$ | DAsp, DGlu, DSer, DAsn, Aad, DBec, Bmc, Bmp, Phe(4COOH), DHyp, DHoSer, DTha, Ahch, Actp, Akch, Tyr(diI), DTrp, DThz, D2Thi, D3Thi, DCit, DHoCit, Aib, Nglu, and DFua |
| $X_7$ (Library 5) | DAsp, DSer, DAsn, Bmp, DHoSer, Nglu, DHoCit, DBec, Aad, DHyp, Ahch, Phe(4COOH), Akch, Aecc, DAbu, DPhe(3,4-diOMe), Cpa, D2Thi, DThz, DPhg, DPhe(4-NO$_2$), DNle, D(NMe)Phe, Aic, DChg, DBta, DBpa, DNal2, DNal1, DTic, Ppca, DCha, DBipa, Deg, and Dpg |
| $X_7$ (Library 6) | Acpc, Bmc, DCit, DGlu, Sar, DTha, DPra, Actp, Aib, DAgl, Acbc, DFua, DVal, DNva, D3Thi, DTrp, DPhe, DIle, DBug, Ach, D(NMe)Val, DCpeg, D(CαMe)Phe, Tyr(diI), DPhe(2-Cl), DBua, DHoPhe, DHoLeu, DSta, DIng, DPhe(4-CF$_3$), Oic, DDpa, DPhe(4-t-Bu), DHoCha, and DPhe(3,4-diCl) |

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound of formula IIa:

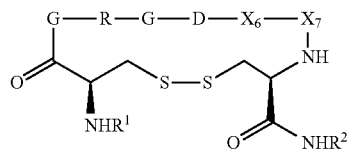

(IIa)

wherein $X_6$ and $X_7$ are each independently a D-amino acid;

$R^1$ is selected from the group consisting of H, $C_{1-6}$ alkyl, and $-C(O)R^{1a}$;

$R^{1a}$ is selected from the group consisting of $C_{1-6}$ alkyl, $C_{1-6}$ heteroalkyl, $C_{1-6}$ alkyl-$NH_2$, $C_{1-6}$ alkyl-$C(O)N(H)-C_{1-6}$ heteroalkyl, cycloalkyl, $C_{1-6}$ alkyl-cycloalkyl, heterocycloalkyl, $C_{1-6}$ alkyl-heterocycloalkyl, aryl, $C_{1-6}$ alkyl-aryl, heteroaryl, and $C_{1-6}$ alkyl-heteroaryl, wherein the cycloalkyl, heterocycloalkyl, heteroaryl and aryl groups are optionally substituted with a member selected from the group consisting of halogen, $-NO_2$, $-OH$, $-CN$, $C_{1-6}$ alkyl, $C_{1-6}$ alkoxy, $C_{1-6}$ haloalkyl and $C_{1-6}$ haloalkoxy; and $R^2$ is selected from the group consisting of H and $C_{1-6}$ alkyl.

2. The compound of claim 1, wherein
$R^1$ and $R^2$ are each independently selected from the group consisting of H and $C_{1-6}$ alkyl.

3. The compound of claim 1, wherein
$X_6$ is selected from the group consisting of DSer, DAsp, DGlu, and DCit; and
$X_7$ is selected from the group consisting of DPhe, DGlu, DSer, DBug, DBta, DVal, DAgl, DPra, D(NMe)Val, D(CαMe)Val, DAbu, DIng, DIle, DTha, DAsp, and DNall.

4. The compound of claim 1, wherein
$X_6$ is selected from the group consisting of DAsp and DSer; and
$X_7$ is selected from the group consisting of DGlu, DPhe, DSer, DVal, DBug and DBta.

5. The compound of claim 1, wherein the compound is selected from the group consisting of cGRGDsfc, cGRGDdfc, cGRGDsec, cGRGDdsc, cGRGDd-DBug-c, cGRGDd-DBta-c, cGRGDdvc, Ac-cGRGDdvc, (β-alanine)-cGRGD-dvc, (Ebes)-cGRGDdvc, cGRGDd-DAgl-c, cGRGDd-DPra-c, cGRGDd-DBug-c, cGRGDd-D(NMe)Val-c, cGRGDd-D(CαMe)Val-c, cGRGDd-DAbu c, cGRGDd-DNall-c, cGRGDd-DNal2-c, and cGRGDd-DBta-c.

6. The compound of claim 1, wherein the compound is selected from the group consisting of cGRGDsfc, cGRGD-dfc, cGRGDsec, cGRGDdsc, cGRGDdvc, cGRGDd-DBug-c and cGRGDd-DBta-c.

7. The compound of claim 1, having formula IIc:

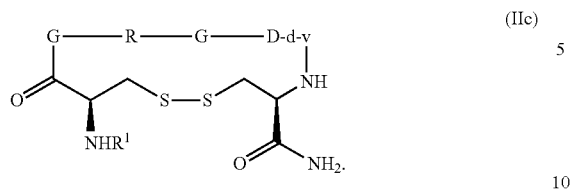

(IIc)

8. The compound of claim 7, wherein the compound is selected from the group consisting of acetyl-cGRGDdvc, 3-amino propanoyl-cGRGDdvc, (Ebes)-cGRGDdvc, isobutyryl-cGRGDdvc, valeryl-cGRGDdvc, cyclohexyl acetyl-cGRGDdvc, 3-phenyl-propionyl-cGRGDdvc, p-chlorophenyl acetyl-cGRGDdvc, 4-nitrobezoyl-cGRGDdvc, 3,5-dihydroxy-benzoyl-cGRGDdvc, 4-(trifluoromethyl) benzoyl-cGRGDdvc, 2-methylthiazole-4-carbonyl-cGRGDdvc, nicotinyl-cGRGDdvc, 2-naphthoyl-cGRGDdvc, and biphenyl-4-carbonyl-cGRGDdvc.

9. A pharmaceutical composition comprising a compound of claim 1 and a pharmaceutically acceptable excipient.

\* \* \* \* \*